United States Patent
Phillips et al.

(10) Patent No.: US 12,268,878 B2
(45) Date of Patent: *Apr. 8, 2025

(54) APPARATUS AND METHODS FOR MAINTAINING PHYSIOLOGICAL FUNCTIONS

(71) Applicant: THE UNIVERSITY OF BRITISH COLUMBIA, Vancouver (CA)

(72) Inventors: Aaron Phillips, Calgary (CA); Andrei Krassioukov, Vancouver (CA); Jordan Squair, Surrey (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 312 days.

This patent is subject to a terminal disclaimer.

(21) Appl. No.: 17/644,765

(22) Filed: Dec. 16, 2021

(65) Prior Publication Data

US 2022/0111208 A1    Apr. 14, 2022

Related U.S. Application Data

(63) Continuation of application No. 16/486,788, filed as application No. PCT/CA2018/050184 on Feb. 16, 2018, now Pat. No. 11,235,154.

(Continued)

(51) Int. Cl.
*A61N 1/36* (2006.01)
*A61B 5/021* (2006.01)
(Continued)

(52) U.S. Cl.
CPC ........ *A61N 1/36117* (2013.01); *A61N 1/0456* (2013.01); *A61N 1/0551* (2013.01);
(Continued)

(58) Field of Classification Search
CPC .............. A61N 1/36117; A61N 1/0456; A61N 1/0551; A61N 1/36031; A61N 1/36034;
(Continued)

(56) References Cited

U.S. PATENT DOCUMENTS 2,868,343 A   1/1959 Sproul
3,543,761 A   12/1970 Bradley
(Continued)

FOREIGN PATENT DOCUMENTS

AU   2012204526 B2   9/2016
CA   2856202 A1   5/2013
(Continued)

OTHER PUBLICATIONS

Anderson, K., "Targeting Recovery: Priorities of the Spinal Cord-Injured Population," Journal of Neurotrauma, vol. 21, No. 10, Oct. 2004, 13 pages.

(Continued)

*Primary Examiner* — Mark W. Bockelman
(74) *Attorney, Agent, or Firm* — McCoy Russell LLP

(57) ABSTRACT

A device and algorithm for controlling an autonomic function in an individual. A controller device that utilizes physiological measurements (such as blood pressure) to regulate spinal cord electrical stimulation to stabilize blood pressure. A control interface and algorithm for controlling an autonomic function in a subject. For instance, an algorithm that utilizes physiological measurements (such as blood pressure) to regulate spinal cord electrical stimulation to stabilize blood pressure.

20 Claims, 20 Drawing Sheets

Related U.S. Application Data

(60) Provisional application No. 62/581,305, filed on Nov. 3, 2017, provisional application No. 62/470,468, filed on Mar. 13, 2017, provisional application No. 62/460,224, filed on Feb. 17, 2017.

(51) Int. Cl.
  *A61N 1/04* (2006.01)
  *A61N 1/05* (2006.01)

(52) U.S. Cl.
  CPC ..... *A61N 1/36031* (2017.08); *A61N 1/36034* (2017.08); *A61N 1/36057* (2013.01); *A61N 1/36139* (2013.01); *A61B 5/021* (2013.01)

(58) Field of Classification Search
  CPC ............ A61N 1/36057; A61N 1/36139; A61N 1/36135; A61B 5/021; A61B 5/4836
  See application file for complete search history.

(56) References Cited

U.S. PATENT DOCUMENTS

| | | |
|---|---|---|
| 3,650,277 A | 3/1972 | Sjostrand et al. |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,398,537 A | 8/1983 | Holmbo |
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss et al. |
| 4,569,352 A | 2/1986 | Petrofsky et al. |
| 4,573,481 A | 3/1986 | Bullara |
| 4,724,842 A | 2/1988 | Charters |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,058,331 A | 5/2000 | King |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Daignault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,340,298 B1 | 3/2008 | Barbut |
| 7,381,192 B2 | 6/2008 | Brodard et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | De Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,051 B2 | 1/2012 | Cross, Jr. et al. |
| 8,108,052 B2 | 1/2012 | Boling |
| 8,131,358 B2 | 3/2012 | Moffitt et al. |

(56) References Cited

U.S. PATENT DOCUMENTS

| | | |
|---|---|---|
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson et al. |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,543,200 B2 | 9/2013 | Lane et al. |
| 8,588,884 B2 | 11/2013 | Hegde et al. |
| 8,626,300 B2 | 1/2014 | Demarais et al. |
| 8,700,145 B2 | 4/2014 | Kilgard et al. |
| 8,712,546 B2 | 4/2014 | Kim et al. |
| 8,740,825 B2 | 6/2014 | Ehrenreich et al. |
| 8,750,957 B2 | 6/2014 | Tang et al. |
| 8,768,481 B2 | 7/2014 | Lane |
| 8,805,542 B2 | 8/2014 | Tai et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| 9,597,517 B2 | 3/2017 | Moffitt |
| 9,610,442 B2 | 4/2017 | Yoo et al. |
| 9,802,052 B2 | 10/2017 | Marnfeldt |
| 9,895,545 B2 | 2/2018 | Rao et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| 10,449,371 B2 | 10/2019 | Serrano Carmona |
| 10,751,533 B2 | 8/2020 | Edgerton et al. |
| 10,773,074 B2 | 9/2020 | Liu et al. |
| 10,806,927 B2 | 10/2020 | Edgerton et al. |
| 10,806,935 B2 | 10/2020 | Rao et al. |
| 11,097,122 B2 | 8/2021 | Lu |
| 11,123,312 B2 | 9/2021 | Lu et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0100933 A1 | 5/2003 | Ayal et al. |
| 2003/0114894 A1 | 6/2003 | Dar et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0070982 A1 | 3/2005 | Heruth et al. |
| 2005/0075669 A1 | 4/2005 | King |
| 2005/0075678 A1 | 4/2005 | Faul |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0231186 A1 | 10/2005 | Saavedra Barrera et al. |
| 2005/0246004 A1 | 11/2005 | Cameron et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0015153 A1 | 1/2006 | Gliner et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0016097 A1 | 1/2007 | Farquhar et al. |
| 2007/0016266 A1 | 1/2007 | Paul, Jr. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0142874 A1 | 6/2007 | John |
| 2007/0150023 A1 | 6/2007 | Ignagni et al. |
| 2007/0156172 A1 | 7/2007 | Alvarado |
| 2007/0156179 A1 | 7/2007 | S. E. |
| 2007/0156200 A1 | 7/2007 | Kornet et al. |
| 2007/0168008 A1 | 7/2007 | Olsen |

(56) References Cited

U.S. PATENT DOCUMENTS

| | | |
|---|---|---|
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0103579 A1 | 5/2008 | Gerber |
| 2008/0105185 A1 | 5/2008 | Kuhlman |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0279896 A1 | 11/2008 | Heinen et al. |
| 2008/0294211 A1 | 11/2008 | Moffitt |
| 2008/0294226 A1 | 11/2008 | Moffitt et al. |
| 2009/0012436 A1 | 1/2009 | Lanfermann et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0229166 A1 | 9/2009 | Sawrie |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0010646 A1 | 1/2010 | Drew et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0070007 A1 | 3/2010 | Parker et al. |
| 2010/0114205 A1 | 5/2010 | Donofrio et al. |
| 2010/0114239 A1 | 5/2010 | McDonald, III |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0280570 A1 | 11/2010 | Sturm et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | Degiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0231326 A1 | 9/2011 | Marino |
| 2011/0237221 A1 | 9/2011 | Prakash et al. |
| 2011/0237921 A1 | 9/2011 | Prakash et al. |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0029528 A1 | 2/2012 | MacDonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0123223 A1 | 5/2012 | Freeman et al. |
| 2012/0123293 A1 | 5/2012 | Shah et al. |
| 2012/0126392 A1 | 5/2012 | Kälvesten et al. |
| 2012/0136408 A1 | 5/2012 | Grill et al. |

(56) References Cited

U.S. PATENT DOCUMENTS

| | | |
|---|---|---|
| 2012/0165899 A1 | 6/2012 | Gliner |
| 2012/0172222 A1 | 7/2012 | Artigas Puerto |
| 2012/0172246 A1 | 7/2012 | Nguyen et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0221073 A1 | 8/2012 | Southwell et al. |
| 2012/0232615 A1 | 9/2012 | Barolat et al. |
| 2012/0252380 A1 | 10/2012 | Kawakita |
| 2012/0252874 A1 | 10/2012 | Feinstein et al. |
| 2012/0259380 A1 | 10/2012 | Pyles |
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0012853 A1 | 1/2013 | Brown |
| 2013/0013041 A1 | 1/2013 | Glukhovsky et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0035745 A1 | 2/2013 | Ahmed et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0237948 A1 | 9/2013 | Donders et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Vörös et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2014/0005753 A1 | 1/2014 | Carbunaru |
| 2014/0031893 A1 | 1/2014 | Walker et al. |
| 2014/0046407 A1 | 2/2014 | Ben-Ezra et al. |
| 2014/0058292 A1 | 2/2014 | Alford et al. |
| 2014/0058490 A1 | 2/2014 | DiMarco |
| 2014/0066950 A1 | 3/2014 | MacDonald et al. |
| 2014/0067007 A1 | 3/2014 | Drees et al. |
| 2014/0067354 A1 | 3/2014 | Kaula et al. |
| 2014/0074190 A1 | 3/2014 | Griffith |
| 2014/0081011 A1 | 3/2014 | Vaught |
| 2014/0081071 A1 | 3/2014 | Simon et al. |
| 2014/0088674 A1 | 3/2014 | Bradley |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0172045 A1 | 6/2014 | Yip et al. |
| 2014/0180361 A1 | 6/2014 | Burdick et al. |
| 2014/0213842 A1 | 7/2014 | Simon et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon De Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0066111 A1 | 3/2015 | Blum et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0196231 A1 | 7/2015 | Ziaie et al. |
| 2015/0217120 A1 | 8/2015 | Nandra et al. |
| 2015/0231396 A1 | 8/2015 | Burdick et al. |
| 2015/0265830 A1 | 9/2015 | Simon et al. |
| 2015/0328462 A1 | 11/2015 | Griffith |
| 2016/0001096 A1 | 1/2016 | Mishelevich |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0143588 A1 | 5/2016 | Hoitink et al. |
| 2016/0157389 A1 | 6/2016 | Hwang |
| 2016/0220813 A1 | 8/2016 | Edgerton et al. |
| 2016/0235977 A1 | 8/2016 | Lu et al. |
| 2016/0175586 A1 | 9/2016 | Edgerton et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0310739 A1 | 10/2016 | Burdick et al. |
| 2017/0007320 A1 | 1/2017 | Levin et al. |
| 2017/0056661 A1 | 3/2017 | Lin et al. |
| 2017/0128729 A1 | 5/2017 | Netoff et al. |
| 2017/0007831 A1 | 6/2017 | Edgerton et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0296837 A1 | 10/2017 | Jin |
| 2017/0354819 A1 | 12/2017 | Bloch et al. |
| 2017/0361093 A1 | 12/2017 | Yoo et al. |
| 2018/0056078 A1 | 3/2018 | Kashyap et al. |
| 2018/0085583 A1 | 3/2018 | Zhang et al. |
| 2018/0104479 A1 | 4/2018 | Grill et al. |
| 2018/0110992 A1 | 4/2018 | Parramon et al. |
| 2018/0125416 A1 | 5/2018 | Schwarz et al. |
| 2018/0178008 A1 | 6/2018 | Bouton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0229037 A1 | 8/2018 | Edgerton et al. |

(56) References Cited

U.S. PATENT DOCUMENTS

| | | |
|---|---|---|
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0280693 A1 | 10/2018 | Edgerton et al. |
| 2018/0353755 A1 | 12/2018 | Edgerton et al. |
| 2018/0361146 A1 | 12/2018 | Gerasimenko et al. |
| 2019/0022371 A1 | 1/2019 | Chang et al. |
| 2019/0033622 A1 | 1/2019 | Olgun et al. |
| 2019/0160294 A1 | 5/2019 | Peterson et al. |
| 2019/0167987 A1 | 6/2019 | Lu et al. |
| 2019/0192864 A1 | 6/2019 | Koop et al. |
| 2019/0247650 A1 | 8/2019 | Tran |
| 2019/0269917 A1 | 9/2019 | Courtine et al. |
| 2019/0381313 A1 | 12/2019 | Lu |
| 2019/0381328 A1 | 12/2019 | Wechter et al. |
| 2020/0155865 A1 | 5/2020 | Lu |
| 2020/0228901 A1 | 7/2020 | Baek |
| 2021/0069052 A1 | 3/2021 | Burke |
| 2021/0187278 A1 | 6/2021 | Lu |
| 2021/0236837 A1 | 8/2021 | Lu |
| 2021/0378991 A1 | 12/2021 | Lu et al. |

FOREIGN PATENT DOCUMENTS

| | | | |
|---|---|---|---|
| CA | 2864473 A1 | 5/2013 | |
| CA | 2823592 A1 | 11/2021 | |
| CN | 101227940 A | 7/2008 | |
| CN | 103263727 A | 8/2013 | |
| CN | 104307098 A | 1/2015 | |
| EP | 0630987 A1 | 12/1994 | |
| EP | 2130326 A1 | 12/2009 | |
| EP | 2141851 A2 | 1/2010 | |
| EP | 2160127 A1 | 3/2010 | |
| EP | 2178319 A1 | 4/2010 | |
| EP | 2192897 A1 | 6/2010 | |
| EP | 2226114 A1 | 9/2010 | |
| EP | 2258496 A1 | 12/2010 | |
| EP | 2361631 A1 | 8/2011 | |
| EP | 2368401 A1 | 9/2011 | |
| EP | 2387467 A1 | 11/2011 | |
| EP | 2396995 A1 | 12/2011 | |
| EP | 2397788 A1 | 12/2011 | |
| EP | 2445990 A2 | 5/2012 | |
| EP | 2471518 A2 | 7/2012 | |
| EP | 2475283 A1 | 7/2012 | |
| EP | 2486897 A2 | 8/2012 | |
| EP | 2626051 A1 | 8/2013 | |
| EP | 2628502 A1 | 8/2013 | |
| EP | 2661307 A2 | 11/2013 | |
| EP | 2688642 A2 | 1/2014 | |
| EP | 2810689 A1 | 12/2014 | |
| EP | 2810690 A1 | 12/2014 | |
| EP | 2868343 A1 | 5/2015 | |
| EP | 2966422 A1 | 1/2016 | |
| EP | 2968940 A1 | 1/2016 | |
| EP | 3184145 A1 | 6/2017 | |
| EP | 3323468 A1 | 5/2018 | |
| EP | 3328481 A1 | 6/2018 | |
| EP | 3527258 A1 | 8/2019 | |
| JP | H0326620 A | 2/1991 | |
| JP | 3184145 B2 | 7/2001 | |
| JP | 2002200178 A | 7/2002 | |
| JP | 2004065529 A | 3/2004 | |
| JP | 2007526798 A | 9/2007 | |
| JP | 2008067917 A | 3/2008 | |
| JP | 2008543429 A | 12/2008 | |
| JP | 2014514043 A | 6/2014 | |
| JP | 2016506255 A | 3/2016 | |
| JP | 6132856 B2 | 4/2017 | |
| JP | 2017104685 A | 6/2017 | |
| JP | 2017525509 A | 9/2017 | |
| JP | 2018524113 A | 8/2018 | |
| RU | 2130326 C1 | 5/1999 | |
| RU | 2141851 C1 | 11/1999 | |
| RU | 2160127 C1 | 12/2000 | |
| RU | 2178319 C2 | 1/2002 | |
| RU | 2192897 C2 | 11/2002 | |
| RU | 2193441 C2 | 11/2002 | |
| RU | 2226114 C1 | 3/2004 | |
| RU | 2258496 C2 | 8/2005 | |
| RU | 2361631 C2 | 7/2009 | |
| RU | 2368401 C1 | 9/2009 | |
| RU | 2387467 C1 | 4/2010 | |
| RU | 2396995 C2 | 8/2010 | |
| RU | 2397788 C2 | 8/2010 | |
| RU | 2445990 C1 | 3/2012 | |
| RU | 2471518 C2 | 1/2013 | |
| RU | 2475283 C2 | 2/2013 | |
| RU | 2661307 C1 | 7/2018 | |
| WO | 97047357 A1 | 12/1997 | |
| WO | 02034331 A2 | 5/2002 | |
| WO | 02092165 A1 | 11/2002 | |
| WO | 03005887 A2 | 1/2003 | |
| WO | 03026735 A2 | 4/2003 | |
| WO | 03092795 A1 | 11/2003 | |
| WO | 2004087116 A2 | 10/2004 | |
| WO | 2005002663 A2 | 1/2005 | |
| WO | 2005051306 A2 | 6/2005 | |
| WO | 2005065768 A1 | 7/2005 | |
| WO | 2005087307 A2 | 9/2005 | |
| WO | 2006138069 A1 | 12/2006 | |
| WO | 2007007058 A1 | 1/2007 | |
| WO | 2007012114 A1 | 2/2007 | |
| WO | 2007047852 A2 | 4/2007 | |
| WO | 2007081764 A1 | 7/2007 | |
| WO | 2007107831 A2 | 9/2007 | |
| WO | 2008070807 A3 | 6/2008 | |
| WO | 2008075294 A1 | 6/2008 | |
| WO | 2008109862 A2 | 9/2008 | |
| WO | 2008121891 A1 | 10/2008 | |
| WO | 2009042217 A1 | 4/2009 | |
| WO | 2009111142 A2 | 9/2009 | |
| WO | 2010021977 A1 | 2/2010 | |
| WO | 2010055421 A1 | 5/2010 | |
| WO | 2010114998 A1 | 10/2010 | |
| WO | 2010124128 A1 | 10/2010 | |
| WO | 2011005607 A1 | 1/2011 | |
| WO | 2011136875 A1 | 11/2011 | |
| WO | 2012050200 A1 | 4/2012 | |
| WO | 2012075195 A1 | 6/2012 | |
| WO | 2012080964 A1 | 6/2012 | |
| WO | 2012094346 A2 | 7/2012 | |
| WO | 2012100260 A1 | 7/2012 | |
| WO | 2012129574 A2 | 9/2012 | |
| WO | 2013071307 A1 | 5/2013 | |
| WO | 2013071309 A1 | 5/2013 | |
| WO | 2013152124 A1 | 10/2013 | |
| WO | 2013179230 A1 | 12/2013 | |
| WO | 2013188965 A1 | 12/2013 | |
| WO | 2014005075 A1 | 1/2014 | |
| WO | 2014031142 A1 | 2/2014 | |
| WO | 2014089299 A2 | 6/2014 | |
| WO | 2014144785 A1 | 9/2014 | |
| WO | 2014149895 A1 | 9/2014 | |
| WO | 2014205356 A2 | 12/2014 | |
| WO | 2014209877 A1 | 12/2014 | |
| WO | 2015000800 A1 | 1/2015 | |
| WO | 2015048563 A2 | 4/2015 | |
| WO | 2015063127 A1 | 5/2015 | |
| WO | 2015106286 A1 | 7/2015 | |
| WO | 2016029159 A2 | 2/2016 | |
| WO | 2016033369 A1 | 3/2016 | |
| WO | 2016033372 A1 | 3/2016 | |
| WO | 2016064761 A1 | 4/2016 | |
| WO | 2016110804 A1 | 7/2016 | |
| WO | 2016112398 A1 | 7/2016 | |
| WO | 2016172239 A1 | 10/2016 | |
| WO | 2017011410 A1 | 1/2017 | |
| WO | 2017024276 A1 | 2/2017 | |
| WO | 2017035512 A1 | 3/2017 | |
| WO | 2017044904 A1 | 3/2017 | |
| WO | 2017058913 A1 | 4/2017 | |
| WO | 2017062508 A1 | 4/2017 | |
| WO | 2017117450 A1 | 7/2017 | |

(56) References Cited

FOREIGN PATENT DOCUMENTS

| WO | 2017146659 A1 | 8/2017 |
|---|---|---|
| WO | 2018039296 A2 | 3/2018 |
| WO | 2018106843 A1 | 6/2018 |
| WO | 2018160531 A1 | 8/2018 |
| WO | 2018217791 A1 | 11/2018 |
| WO | 2019211314 A1 | 11/2019 |
| WO | 2020041502 A1 | 2/2020 |
| WO | 2020041633 A1 | 2/2020 |
| WO | 2020236946 A1 | 11/2020 |

OTHER PUBLICATIONS

Krassioukov, A. et al., "A Systematic Review of the Management of Autonomic Dysreflexia Following Spinal Cord Injury," Archives of Physical Medicine and Rehabilitation, vol. 90, No. 4, Apr. 2009, 27 pages.

Krassioukov, A. et al., "A Systematic Review of the Management of Orthostatic Hypotension Following Spinal Cord Injury," Archives of Physical Medicine and Rehabilitation, vol. 90, No. 5, May 2009, 22 pages.

Wan, D. et al., "Life-threatening outcomes associated with autonomic dysreflexia: A clinical review," Journal of Spinal Cord Medicine, vol. 37, No. 1, Jan. 2014, 9 pages.

Phillips, A. et al., "Perturbed and spontaneous regional cerebral blood flow responses to changes in blood pressure after high-level spinal cord injury: the effect of midodrine," Journal of Applied Physiology, vol. 116, No. 6, Mar. 15, 2014, Available Online Jan. 16, 2014, 20 pages.

Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, May 2014, 8 pages.

Phillips, A. et al., "Contemporary Cardiovascular Concerns after Spinal Cord Injury: Mechanisms, Maladaptations, and Management," Journal of Neurotrama, vol. 32, No. 24, Dec. 15, 2015, 17 pages.

Robbins, H., "Some Aspects of the Sequential Design of Experiments," Bulletin of the American Mathematical Society, vol. 58, Sep. 1, 1952, 9 pages.

Minoux, M., "Accelerated greedy algorithms for maximizing submodular set functions," Optimization Techniques, Proceedings of the LNCIS, vol. 7, 1978, 10 pages.

Gittins, J. C., "Bandit Processes and Dynamic Allocation Indices," Journal of the Royal Statistical Society B, vol. 41, No. 2, Jan. 1979, 17 pages.

Harrison, P. et al., "Individual Excitatory Post-Synaptic Potentials Due to Muscle Spindle la Afferents in Cat Triceps Surae Motoneurones," The Journal of Physiology, vol. 312, No. 1, Mar. 1981, 16 pages.

Lovely, R. et al., "Effects of Training on the Recovery of Full-Weight-Bearing Stepping in the Adult Spinal Cat," Experimental Neurology, vol. 92, No. 2, May 1986, 15 pages.

Barbeau, H. et al., "Recovery of locomotion after chronic spinalization in the adult cat," Brain Research, vol. 412, No. 1, May 26, 1987, 12 pages.

Colgate, E. et al., "An Analysis of Contact Instability in Terms of Passive Physical Equivalents," Proceedings of the 1989 IEEE International Conference on Robotics and Automation, Scottsdale, Arizona, May 14, 1989, 6 pages.

Wernig, A. et al., "Laufband locomotion with body weight support improved walking in persons with severe spinal cord injuries," Paraplegia, vol. 30, No. 4, Apr. 1992, 10 pages.

Pratt, J. et al., "Series elastic actuators for high fidelity force control," Industrial Robot: An International Journal, vol. 29, No. 3, Available as Early as Jan. 1, 2002, 13 pages.

Winter, D. A. et al., "An integrated EMG/biomechanical model of upper body balance and posture during human gait," Progress in Brain Research, vol. 97, Ch. 32, Available as Early as Jan. 1, 1993, 9 pages.

Pratt, G. et al., "Stiffness Isn't Everything," Proceedings of the Fourth International Symposium on Experimental Robotics, Jun. 30, 1995, Stanford, California, 6 pages.

Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.

Harkema, S. et al., "Human Lumbosacral Spinal Cord Interprets Loading During Stepping," Journal of Neurophysiology, vol. 77, No. 2, Feb. 1, 1997, 15 pages.

Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.

Jones, D. R. et al., "Efficient Global Optimization of Expensive Black-Box Functions," Journal of Global Optimization, vol. 13, 1998, 38 pages.

Dimitrijevic, M. M. et al., "Evidence for a Spinal Central Pattern Generator in Humans," Annals New York Academy Sciences, vol. 860, 1998, 17 pages.

Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.

Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.

Kirkwood, P., "Neuronal Control of Locomotion: From Mollusk to Man—G.N. Orlovsky, T.G. Deliagina and S. Grillner, Oxford University Press," Clinical Neurophysiology, vol. 111, No. 8, Published Online Jul. 17, 2000, Aug. 1, 2000, 2 pages.

Murg, M. et al., "Epidural electric stimulation of posterior structures of the human lumbar spinal cord: 1. Muscle twitches—a functional method to define the site of stimulation." Spinal Cord, vol. 38, 2000, 9 pages.

Auer, P. et al., "Finite-time Analysis of the Multiarmed Bandit Problem," Machine Learning, vol. 47, No. 2, 2002, 22 pages.

Auer, P. "Using Confidence Bounds for Exploitation-Exploration Trade-offs," Journal of Machine Learning Research, vol. 3, 2002, 26 pages.

Dimitrijevic, M. et al., "Clinical Elements for the Neuromuscular Stimulation and Functional Electrical Stimulation protocols in the Practice of Neurorehabilitation," Artificial Organs, vol. 26, No. 3, 2002, 4 pages.

Gerasimenko, Y. et al., "Control of Locomotor Activity in Humans and Animals in the Absence of Supraspinal Influences," Neuroscience and Behavioral Physiology, vol. 32, No. 4, 2002, 7 pages.

Herman, R. et al., "Spinal cord stimulation facilitates functional walking in a chronic, incomplete spinal cord injured," Spinal Cord, vol. 40, No. 2, 2002, 4 pages.

Yakovenko, S. et al., "Spatiotemporal Activation of Lumbosacral Motoneurons in the Locomotor Step Cycle," Journal of Neurophysiology, vol. 87, No. 3, Mar. 2002, 12 pages.

Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, 11 pages.

Steward, O. et al., "False Resurrections: Distinguishing Regenerated from Spared Axons in the Injured Central Nervous System," The Journal of Comparative Neurology, vol. 459, No. 1, Apr. 21, 2003, 8 pages.

Minassian, K. et al., "Stepping-like movements in humans with complete spinal cord injury induced by epidural stimulation of the lumbar cord: electromyographic study of compound muscle action potentials", Spinal Cord, vol. 42, 2004, 16 pages.

Pearson, K., "Generating the walking gait: role of sensory feedback," Progress in Brain Research, vol. 143, Chapter 12, Published Online Nov. 28, 2003, 2004, 7 pages.

Rasmussen, C., "Gaussian Processes in Machine Learning", L.N. A.I., vol. 3176, 2003, 9 pages.

Carhart, M. et al., "Epidural Spinal-Cord Stimulation Facilitates Recovery of Functional Walking Following Incomplete Spinal-Cord

(56) References Cited

OTHER PUBLICATIONS

Injury," IEEE Transactions on Neural Systems and Rehabilitation Engineering, vol. 12, No. 1, Mar. 15, 2004, 11 pages.
Bareyre, F. et al., "The injured spinal cord spontaneously forms a new intraspinal circuit in adult rats," Nature Neuroscience, vol. 7, No. 3, Published Online Feb. 15, 2004, Mar. 2004, 9 pages.
Dimitrijevic, M. et al., "Electrophysiological characteristics of H-reflexes elicited by percutaneous stimulation of the cauda equina," Abstract No. 4927, Proceedings of the 34th Annual Meeting of the Society for Neuroscience, San Diego, California, 2004, 1 page.
Jilge, B. et al., "Initiating extension of the lower limbs in subjects with complete spinal cord injury by epidural lumbar cord stimulation," Experimental Brain Research, vol. 154, 2004, 19 pages.
Ganley, K. et al., "Epidural Spinal Cord Stimulation Improves Locomotor Performance in Low ASIA C, Wheelchair-Dependent, Spinal Cord-Injured Individuals: Insights from Metabolic Response," Topics in Spinal Cord Injury Rehabilitation, vol. 11, No. 2, 2005, 14 pages.
Krause, A. et al., "Near-optimal Nonmyopic Value of Information in Graphical Models," Proceedings of the Twenty-First Conference on Uncertainty in Artificial Intelligence (UAI'05), 2005, Edinburgh, Scotland, 8 pages.
Minassian, K. et al., "Peripheral and central afferent input to the lumbar cord," Biocybemetics and Biomedical Engineering, vol. 25, No. 3, 2005, 19 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Published Online May 4, 2005, Aug. 1, 2005, 13 pages.
Timozyk, W. et al., "Hindlimb loading determines stepping quantity and quality following spinal cord transection," Brain Research, vol. 1050, No. 1-2, Published Online Jun. 24, 2005, Jul. 19, 2005, 10 pages.
Wernig, A., "Ineffectiveness■ of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Rasmussen, C. et al., "Gaussian Processes for Machine Learning," The MIT Press, Cambridge, Massachusetts, 2006, 266 pages.
Pudo, D. et al., "Estimating Intensity Fluctuations in High Repetition Rate Pulse Trains Generated Using the Temporal Talbot Effect," IEEE Photonics Technology Letters, vol. 18, No. 5, Mar. 1, 2006, 3 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Kocsis, L. et al. "Bandit Based Monte-Carlo Planning," Proceedings of the European Conference on Machine Learning, Springer, Berlin, Heidelberg, Sep. 2006, 12 pages.
Fleshman, J. et al., "Electronic Architecture of Type-Identified a-Motoneurons in the Cat Spinal Cord," Journal of Neurophysiology, vol. 60, No. 1, Jul. 1, 1988, 26 pages.
Jones, K. et al., "Computer Simulation of the Responses of Human Motoneurons to Composite 1A EPSPS: Effects of Background Firing Rate," The Journal of Physiology, vol. 77, No. 1, 1997, 16 pages.
Hines, M. et al., "The Neuron Simulation Environment," Neural Computation, vol. 9, No. 6, Aug. 15, 1997, 26 pages.
Prochazka, A. et al., "Ensemble firing of muscle afferents recorded during normal locomotion in cats," The Journal of Physiology, vol. 507, No. 1, Feb. 15, 1998, 12 pages.

Prochazka, A. et al., "Models of ensemble filing of muscle spindle afferents recorded during normal locomotion in cats," The Journal of Physiology, vol. 507, No. 1, Feb. 15, 1998, 15 pages.
Rattay, F. et al., "Epidural electrical stimulation of posterior structures of the human lumbosacral cord: 2. Quantitative analysis by computer modeling," Spinal Cord, vol. 38, 2000, 17 pages.
Mcintyre, C. et al., "Modeling the Excitability of Mammalian Nerve Fibers: Influence of Afterpotentials on the Recovery Cycle," Journal of Neurophysiology, vol. 87, No. 2, Feb. 2002, 12 pages.
Minassian, K. et al., "Human lumbar cord circuitries can be activated by extrinsic tonic input to generate locomotor-like activity," Human Movement Science, vol. 26, No. 2, 2007, 21 pages.
Rodger, D. et al., "High Density Flexible Parylene-Based Multielectrode Arrays for Retinal and Spinal Cord Stimulation," Proceedings of the 14th International Conference on Solid-State Sensors, Actuators and Microsystems, 2007, pp. 4 pages.
Stienen, A. et al., "Analysis of reflex modulation with a biologically realistic neural network," Journal of Computer Neuroscience, vol. 23, No. 3, Dec. 2007, Available Online May 15, 2007, 16 pages.
Johnson, W. et al., "Application of a Rat Hindlimb Model: A Prediction of Force Spaces Reachable Through Stimulation of Nerve Fascicles," IEEE Transactions on Bio-Medical Engineering, vol. 58, No. 12, Dec. 2011, Available Online Jan. 17, 2011, 22 pages.
Van Den Brand, R. et al., "Restoring Voluntary Control of Locomotion after Paralyzing Spinal Cord Injury," Science Magazine, vol. 336, No. 6085, Jun. 1, 2012, 5 pages.
Hennig, P. et al., "Entropy search for information-efficient global optimization," Journal of Machine Learning Research (JMLR), vol. 13, Jun. 2012, 29 pages.
Gilja, V. et al., "A high-performance neural prosthesis enabled by control algorithm design," Nature Neuroscience, vol. 15, No. 12, Dec. 2012, Published Online Nov. 18, 2012, 56 pages.
Minassian, K. et al., "Neuromodulation of lower limb motor control in restorative neurology," Clinical Neurology and Neurosurgery, vol. 114, 2012, 9 pages.pp. 489-497.
Ryzhov, I. et al., "The knowledge gradient algorithm for a general class of online learning problems," Operations Research, vol. 60, No. 1, 2012, 47 pages.
Azimi, J. et al., "Hybrid Batch Bayesian Optimization," Proceedings of the 29th International Conference on Machine Learning, 2012, Edinburgh, Scotland, 12 pages.
Azimi, J. et al., "Batch Active Learning via Coordinated Matching," Proceedings of the 29th International Conference on Machine Learning, 2012, Edinburgh, Scotland, 8 pages.
Lozano, A. et al., "Probing and Regulating Dysfunctional Circuits Using Deep Brain Stimulation," Neuron, vol. 77, No. 3, Feb. 6, 2013, 19 pages.
Minassian et al., "Mechanisms of rhythm generation of the human lumbar spinal cord in repose to tonic stimulation without and with step-related sensory feedback," Biomedizinische Technik, vol. 58, (Suppl. 1), 2013, 3 pages.
Capogrosso, M. et al., "A Computational Model for Epidural Electrical Stimulation of Spinal Sensorimotor Circuits", Journal of Neuroscience, vol. 33, No. 49, Dec. 4, 2013, 15 pages.
Sayenko, D. et al., "Neuromodulation of evoked muscle potentials induced by epidural spinal-cord stimulation in paralyzed individuals," Journal of Neurophysiology, vol. 111, No. 5, 2014, Published Online Dec. 11, 2013, 12 pages.
Hofstoetter, U. et al., "Effects of transcutaneous spinal cord stimulation on voluntary locomotor activity in an incomplete spinal cord injured individual," Biomed Tech, vol. 58 (Suppl. 1), 2013, 3 pages.
Nandra, M. et al., "Microelectrode Implants for Spindal Cord Stimulation in Rats," Doctor of Philosophy Thesis, California Institute of Technology, 2014, 104 pages.
Angeli, C. et al., "Altering spinal cord excitability enables voluntary movements after chronic complete paralysis in humans," Brain, vol. 137, No. 5, May 2014, Available Online Apr. 8, 2014, 16 pages.
Zhang, T. et al., "Mechanisms and models of spinal cord stimulation for the treatment of neuropathic pain," Brain Research, vol. 1569, Jun. 20, 2014, Published Online May 4, 2014, 14 pages.

(56) References Cited

OTHER PUBLICATIONS

Wenger, N. et al. "Closed-loop neuromodulation of spinal sensorimotor circuits controls refined locomotion after complete spinal cord injury," Science Translational Medicine, Sep. 24, 2014, vol. 6, No. 255, 10 pages.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Takeoka, A. et al., "Muscle Spindle Feedback Directs Locomotor Recovery and Circuit Reorganization after Spinal Cord Injury," Cell, vol. 159, No. 7, Dec. 18, 2014, 27 pages.
Hofstoetter, U. et al., "Modification of spasticity by transcutaneous spinal cord stimulation in individuals with incomplete spinal cord injury," The Journal of Spinal Cord Medicine, vol. 37, No. 2, 2014, 10 pages.
Minev, I. et al., "Electronic dura mater for long-term multimodal neural interfaces," Science Magazine, vol. 347, No. 6218, Jan. 9, 2015, 64 pages.
Gerasimenko, Y. et al., "Noninvasive Reactivation of Motor Descending Control after Paralysis," Journal of Neurotrauma, vol. 32, 2015, 13 pages.
Danner, S. et al., "Human spinal locomotor control is based on flexibly organized burst generators," Brain, vol. 138, No. 3, Mar. 2015, Available Online Jan. 12, 2015, 12 pages.
Rejc, E. et al., "Effects of Lumbosacral Spinal Cord Epidural Stimulation for Standing after Chronic Complete Paralysis in Humans," PLoS One, vol. 10, No. 7, Jul. 24, 2015, 20 pages.
Shamir, R. et al., "Machine Learning Approach to Optimizing Combined Stimulation and Medication Therapies for Parkinson's Disease," Brain Stimulation, vol. 8, No. 6, Nov. 2015, Published Online Jun. 15, 2015, 22 pages.
Jarosiewicz, B. et al., "Virtual typing by people with tetraplegia using a self-calibrating intracortical brain-computer interface," Science Translational Medicine, vol. 7, No. 313, Nov. 11, 2015, 11 pages.
Jarosiewicz, B. et al., "Supplementary Materials for Virtual typing by people with tetraplegia using a self-calibrating intracortical brain-computer interface," Science Translational Medicine, vol. 7, No. 313, Nov. 11, 2015, 26 pages.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Published Online Feb. 4, 2016, 15 pages.
Danner, S. M. et al., "Body Position Influences Which neural structures are recruited by lumbar transcutaneous spinal cord stimulation", PLoS One, vol. 11, No. 1, 2016, 13 pages.
Burke, R., "Group Ia Synaptic Input to Fast and Slow Twitch Motor Units of Cat Triceps Surae," The Journal of Physiology, vol. 196, vol. 3, Jun. 1, 1968, 26 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord injury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2007, Published Online Aug. 22, 2007, 13 pages.
Edgerton, V. et al., "Training Locomotor Networks," Brain Research Reviews, vol. 57, Jan. 2008, Published Online Sep. 16, 2007, 25 pages.
Kwakkel, G. et al., "Effects of Robot-assisted therapy on upper limb recovery after stroke: A Systematic Review," Neurorehabilitation and Neural Repair, vol. 22, No. 2, Mar. 2008, Published Online Sep. 17, 2007, 17 pages.

Lizotte, D. et al., "Automatic gait optimization with Gaussian process regression," Proceedings of the 20th international joint conference on Artifical intelligence (IJCAI), Jan. 6, 2007, Hyderabad, India, 6 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Krause, A. et al. "Near-Optimal Sensor Placements in Gaussian Processes: Theory, Efficient Algorithms and Empirical Studies," Journal of Machine Learning Research (JMLR), vol. 9, Feb. 2008, 8 pages.
Lavrov, I. et al., "Epidural Stimulation Induced Modulation of Spinal Locomotor Networks in Adult Spinal Rats," Journal of Neuroscience, vol. 28, No. 23, Jun. 4, 2008, 8 pages.
Vallery, H. et al., "Compliant Actuation of Rehabilitation Robots," IEEE Robotics & Automation Magazine, vol. 15, No. 3, Sep. 12, 2008, 10 pages.
Abernethy, J. et al., "Competing in the Dark: An Efficient Algorithm for Bandit Linear Optimization," Conference on Learning Theory, 2008, 13 pages.
Bubeck, S. et al., "Online Optimization in X-Armed Bandits," Advances in Neural Information Processing Systems (NIPS), 2008, 8 pages.
Ward, A. R., "Electrical Stimulation Using Kilohertz-Frequency Alternating Current," Physical Therapy, vol. 89, 2009, Published online Dec. 18, 2008, 10 pages.
Dani, V. et al., "Stochastic Linear Optimization Under Bandit Feedback," Proceedings of the 21st Annual Conference on Learning Theory (COLT), 2008, Helsinki, Finland, 15 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Hofstoetter, U. et al., "Modification of Reflex Responses to Lumbar Posterior Root Stimulation by Motor Tasks in Healthy Subjects," Artificial Organs, vol. 32, No. 8, 2008, 5 pages.
Kleinberg, R. et al., "Multi-armed bandits in metric spaces," Proceedings of the STOC, Computer and Automation Research Institute of the Hungarian Academy of Sciences, Budapest, Hungary, 2008, 26 pages.
Brochu, E. et al., "A Tutorial on Bayesian Optimization of Expensive Cost Functions, with Application to Active User Modeling and Hierarchical Reinforcement Learning," TR-2009-23, UBC, 2009, 49 pages.
Bubeck, S. et al., "Pure Exploration in Finitely-Armed and Continuous-Armed Bandits problems," ALT, 2009, 35 pages.
Fuentes, R. et al., "Spinal Cord Stimulation Restores Locomotion in Animal Models of Parkinson's Disease," Science, vol. 323, No. 5921, Mar. 20, 2009, 14 pages.
Hofstoetter, U. et al., "Model of spinal cord reflex circuits in humans: Stimulation frequency-dependence of segmental activities and their interactions," Proceedings of the Second Congress International Society of Intraoperative Neurophysiology (ISIN), Dubrovnik, Croatia, 2009, 149 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.
Minassian, K. et al., "Posterior root-muscle reflex," Proceedings of the Second Congress International Society of Intraoperative Neurophysiology (ISIN), Dubrovnik, Croatia, 2009, 6 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.

(56) References Cited

OTHER PUBLICATIONS

Azimi, J. et al., "Batch Bayesian Optimization via Simulation Matching," Proceedings of the Advances in Neural Information Processing Systems (NIPS), 2010, Vancouver, British Columbia, Canada, 9 pages.

Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.

Wessels, M. et al., "Body Weight-Supported Gait Training for Restoration of Walking in People with an Incomplete Spinal Cord Injury: A Systematic Review," Journal of Rehabilitation Medicine, vol. 42, No. 6, Jun. 2010, 7 pages.

Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.

Ladenbauer, J. et al., "Stimulation of the human lumbar spinal cord with implanted and surface electrodes: a computer simulation study," IEEE Transactions on Neural Systems and Rehabilitation Engineering, vol. 18, No. 6, 2010, 9 pages.

Minassian, K. et al., "Transcutaneous stimulation of the human lumbar spinal cord: Facilitating locomotor output in spinal cord injury," Proceedings of the Society for Neuroscience, Conference Proceedings, Neuroscience 2010, San Diego, CA, Abstract Viewer/Itinerary Planner No. 286. 19, Abstract & Poster Attached, 2010, 1 page.

Rasmussen, C. E. et al., "Gaussian Processes for Machine Learning (GPML) Toolbox," The Journal of Machine Learning Research, vol. 11, 2010, 9 pages.

Widmer, C. et al., "Inferring latent task structure for multitask learning by multiple kernel learning," BMC Bioinformatics, vol. 11, Suppl 8:S5, 2010, 8 pages.

Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.

Srinivas, N. et al., "Gaussian process optimization in the bandit setting: No. regret and experimental design," Proceedings of the 27th International Conference on Machine Learning, 2010, Haifa, Israel, 17 pages.

Tenne, Y. et al., "Computational Intelligence in Expensive Optimization Problems," Adaptation, Learning, and Optimization, vol. 2, Springer, Berlin Heidelberg, 2010, 32 pages.

Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.

Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.

Hidler, J. et al., "ZeroG: Overground gait and balance training system," Journal of Rehabilitation Research & Development, vol. 48, No. 4, Available as Early as Jan. 1, 2011, 12 pages.

Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.

Krause, A. et al. "Contextual Gaussian Process Bandit Optimization", In Advances in Neural Information Processing Systems (NIPS), 2011, 9 pages.

Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.

Wirz, M. et al., "Effectiveness of automated locomotor training in patients with acute incomplete spinal cord injury: A randomized controlled multicenter trial," BMC Neurology, vol. 11, No. 60, May 27, 2011, 9 pages.

Musienko, P. et al., "Controlling specific locomotor behaviors through multidimensional monoaminergic modulation of spinal circuitries," The Journal of Neuroscience, vol. 31, No. 25, Jun. 22, 2011, 32 pages.

Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.

Nandra, M. S. et al., "A parylene-based microelectrode array implant for spinal cord stimulation in rats," Proceedings of the IEEE Engineering in Medicine and Biology Society, 2011, Boston, Massachusetts, 13 pages.

Sun, F. et al., "Sustained axon regeneration induced by co-deletion of PTEN and SOCS3," Nature, vol. 480, No. 7377, Dec. 15, 2011, Published Online Nov. 6, 2011, 12 pages.

APPARATUS AND METHODS FOR MAINTAINING PHYSIOLOGICAL FUNCTIONS

CROSS-REFERENCE TO RELATED APPLICATIONS

The present application is a continuation of U.S. Non-Provisional patent application Ser. No. 16/486,788, entitled "APPARATUS AND METHODS FOR MAINTAINING PHYSIOLOGICAL FUNCTIONS", and filed on Aug. 16, 2019. U.S. Non-Provisional patent application Ser. No. 16/486,788 is a U.S. National Phase of International Application No. PCT/CA2018/050184 entitled "APPARATUS AND METHODS FOR MAINTAINING PHYSIOLOGICAL FUNCTIONS", filed Feb. 16, 2018. International Application No. PCT/CA2018/050184 claims benefit of U.S. Provisional Application No. 62/460,224 filed Feb. 17, 2017 and entitled SERVO-CONTROLLED DEVICE TO MAINTAIN PHYSIOLOGICAL FUNCTIONING, U.S. Provisional Application No. 62/470,468 filed Mar. 13, 2017 and entitled SERVO CONTROLLED INTERFACE TO CONTROL ELECTRICAL STIMULATION FOR RESTORING PHYSIOLOGICAL FUNCTIONING, and U.S. Provisional Application No. 62/581,305 filed Nov. 3, 2017 and entitled SERVO CONTROLLED INTERFACE TO CONTROL ELECTRICAL STIMULATION FOR RESTORING PHYSIOLOGICAL FUNCTIONING. The entire contents of each of the above-listed applications are hereby incorporated by reference for all purposes.

TECHNICAL FIELD

The present disclosure generally relates to the field of bionic interphases. More specifically, the disclosure relates to machine control of physiological functions by way of controlled stimulation (e.g. electrical stimulation). The disclosure has example applications for treating hypotension (low blood pressure) in subjects affected by spinal cord injury.

BACKGROUND

Spinal cord injury (SCI) results in disconnection of some, most, or all descending sympathetic pathways that carry signals responsible for regulating blood pressure. When arterial blood pressure drops or increases following SCI, the spinal cord neurons responsible for blood pressure control no longer have the capacity to maintain blood pressure at a normal physiological level. This disconnection of sympathetic pathways can lead to a situation where blood vessels do not maintain appropriate tone (e.g. the blood vessels can become dilated). As a result, subjects affected by SCI can suffer from extreme hypotension (very low blood pressure). Large amounts of blood may pool in subjects' legs and gut.

Individuals with SCI are often unable to regulate their blood pressure and typically experience a very low arterial blood pressure at rest, during exercise and/or when assuming a seated or standing position. This hypotension can lead to dizziness, disorientation, reduction in cognitive functioning, loss of consciousness and a predisposition to strokes and heart attacks. On the other hand, dangerous elevations in blood pressure (hypertension) can also result from SCI. Hypertension can lead to heart attacks, strokes, and sub-clinical vascular consequences.

Despite widespread misconceptions, autonomic and cardiovascular dysfunctions following SCI are a top health priority (above walking again) and are a main cause of death for individuals with SCI. One primary autonomic issue after high-level SCI (i.e., above the 6th thoracic segment) is orthostatic hypotension, which is clinically-defined as a ≥20 mmHg decrease in systolic blood pressure and/or a 10 mmHg decrease in diastolic blood pressure when assuming the upright posture.

Another critical autonomic issue after SCI is autonomic dysreflexia, which is associated with potentially life threatening elevations in blood pressure due to afferent input activating sympathetic circuitry located caudally on the spinal cord to the location of the SCI. Clinically, autonomic dysreflexia is defined as elevations in systolic blood pressure of 20 mmHg or more.

Currently, the main options for managing blood pressure lability after SCI are pharmacological agents that either can increase or decrease blood pressure. However, most pharmacological tools available for managing orthostatic hypotension and autonomic dysreflexia have significant side effects, as well as a delayed onset of action (at least 10 minutes for drugs to manage high blood pressure, and 60 minutes or more for drugs that manage low blood pressure), and therefore are sub-optimal for managing transient (seconds), but drastic, changes in blood pressure that occur after SCI and other neurological conditions such as multiple sclerosis, autonomic failure, autonomic neuropathy, as well as cancer of the neurological tissue. Importantly, the effects of some of the antihypertensive drugs (e.g. for management of autonomic dysreflexia) can result in a significant decrease in arterial blood pressure, below the desired level, which can last for hours and requires monitoring and further management. As such, pharmacological intervention is often ineffective and can predispose an individual with SCI to extreme changes in blood pressure. Alternative options for controlling blood pressure without the adverse effects inherent to current pharmacological therapies are therefore needed.

The following references provide background to the technology described in the present application:

1. Phillips A A, Krassioukov A V. Contemporary cardiovascular concerns after spinal cord injury: Mechanisms, maladaptations & management. Journal of Neurotrauma. 2015; 32:1927-42.
2. Anderson K D. Targeting recovery: priorities of the spinal cord-injured population. Journal of Neurotrauma. 2004; 21:1371-1383.
3. Wan D, Krassioukov A V. Life-threatening outcomes associated with autonomic dysreflexia: A clinical review. The journal of spinal cord medicine. 2014; 37:2-10.
4. Krassioukov A, Warburton D E, Teasell R, Eng J J. A Systematic Review of the Management of Autonomic Dysreflexia After Spinal Cord Injury. Archives of physical medicine and rehabilitation. 2009; 90:682-695.
5. Krassioukov A, Eng J J, Warburton D E, Teasell R. A systematic review of the management of orthostatic hypotension after spinal cord injury. Arch Phys Med Rehabil. 2009; 90:876-885.
6. Phillips A A, Krassioukov A V, Ainslie P N, Warburton D E R. Perturbed and spontaneous regional cerebral blood flow responses to changes in blood pressure after high level spinal cord injury: the effect of midodrine. Journal of applied physiology (Bethesda, Md: 1985). 2014; 116: 645-653.
7. Phillips A A, Warburton D E R, Ainslie P N, Krassioukov A V. Regional neurovascular coupling and cognitive performance in those with low blood pressure secondary to high-level spinal cord injury: improved by alpha-1 agonist midodrine hydrochloride. Journal of Cerebral Blood Flow & Metabolism. 2014; 34:794-801.

Patent literature in the general field of the present technology includes:

US20110202107A1 2011 Aug. 18 BLOOD PRESSURE STABILIZATION SYSTEM USING TRANSDERMAL STIMULATION describes electric stimulation apparatus for treating hypotension of patients with spinal cord injury and a method for treating hypotension. The apparatus comprises: a blood pressure measuring means for continuously measuring a blood pressure of a subject; an electric current application means for intermittently applying an electric current to skin of the subject; and a control means for controlling the electric current application means so as to maintain the blood pressure at a predetermined target blood pressure value by activating the electric current application means when the subject blood pressure is equal to or less than the target blood pressure value.

JP2004065529A 2004 Mar. 4 BLOOD PRESSURE CONTROLLING APPARATUS describes a blood pressure controlling apparatus which controls a blood pressure in place of a blood pressure control center of the brain without relying on administration of a hypertensor into a vein or blood transfusion. The apparatus has a blood pressure sensor for detecting a blood pressure value of a living body and an electric stimulation part outputting stimulative electricity to be given to the spinal sympathetic nervous system of the living body. A stimulation frequency control part which calculates the stimulation frequency of a stimulative electricity that needs to be given to the spinal sympathetic nervous system of the living body for raising the blood pressure value of the living body to a target set value. A pulse current output part which outputs the stimulative electricity of the stimulation frequency calculated by the control part.

US20130237948A1 2013 Sep. 12 DEVICES FOR REGULATION OF BLOOD PRESSURE AND HEART RATE describe devices for regulation of blood pressure and heart rate which involve applying electrical treatment signals selected to at least partially block nerve impulses, or in some embodiments, to augment nerve impulses. The apparatus provides a therapy program to provide a downregulating signal to one or more nerves including renal artery, renal nerve, vagus nerve, celiac plexus, splanchnic nerve, cardiac sympathetic nerves, and spinal nerves originating between T10 to L5. In embodiments, the apparatus provides a therapy program to provide an upregulating signal to one or more nerves including a glossopharyngeal nerve and/or a tissue containing baroreceptors.

US20130289650A1 2013 Oct. 31 Neuromodulation for Hypertension Control describes use of neuromodulation for controlling hypertension and other cardiorenal disorders of a patient. A neuromodulation device is configured to be delivered to a patient's body and to apply an electric activation to decrease renal sympathetic hyperactivity of the patient based on monitored blood pressure of the patient, substantially without thermal energization of the patient's body by applying the electric activation. The electric activation may also depend on monitored blood volume of the patient. A feedback control module may be used to provide feedback control information for adjusting the electric activation based on the monitored blood pressure and volume of the patient.

WO2017146659A1 2017 Aug. 31 A SYSTEM FOR DECREASING THE BLOOD PRESSURE describes a blood pressure decreasing system that decreases blood pressure of a patient by non-invasively blocking the sympathetic innervation of the kidney;

US20170056661A1 2017 Mar. 2 METHOD OF REDUCING RENAL HYPERTENSION AND COMPUTER-READABLE MEDIUM describes a method of reducing renal hypertension by applying stimulation to a target zone of an organism using an electronic stimulation device.

US20170007320A1 2017 Jan. 12 RENAL NEUROMODULATION FOR TREATMENT OF PATIENTS and U.S. Pat. No. 9,314,630 B2 2016 Apr. 19 describes a method and apparatus for treatment of heart failure, hypertension and renal failure by stimulating the renal nerve.

U.S. Pat. No. 8,740,825 B2 2014 Jun. 3 Methods and devices for treating hypertension describes devices, systems and methods which control blood pressure and nervous system activity by stimulating baroreceptors and/or nerves to reduce blood pressure.

US20130296965A1 2013 Nov. 7 METHOD FOR BLOOD PRESSURE MODULATION USING ELECTRICAL STIMULATION OF THE CORONARY BARORECEPTORS describes apparatus comprising a first stimulation circuit and a control circuit. The stimulation circuit is configured to be electrically coupled to a first electrode assembly that is configured to deliver electrical sub-myocardial activation stimulation to a coronary baroreceptor from a location within a left atrial appendage of a heart.

There remains a need for apparatus and methods that can help people who are suffering from dysregulated autonomic functions as a result of SCI.

SUMMARY

The present disclosure describes technology that has a number of aspects. These aspects may be applied in combination with one another but may also have individual application. These aspects include, without limitation:

A device and algorithm for controlling an autonomic process in a subject using electrical stimulation. The device and algorithm of the present disclosure are based on the surprising discovery that the electrical excitation of spinal cord circuitry caudal to SCI can control the activity of disconnected sympathetic circuitry to regulate blood pressure.

A method performed by a device for generating control signals for a stimulation device.

Methods for regulating blood pressure in subjects affected by SCI. The methods may be effective to alleviate hypotension in such subjects.

Methods for controlling stimulation delivery devices to generate stimulation that may be effective for controlling one or more autonomic functions in a subject.

A system and methods for controlling one or more autonomic functions in a subject.

A method for medical treatment of a subject affected by SCI.

A device according to an example embodiment comprises a processing unit and circuitry that may be configured such that the device may act as an interface between 1) a physiological monitor (e.g., a blood pressure monitor), and 2) a stimulation device (e.g. an electrical stimulation assembly). The device may interface with a variety of physiological monitors and stimulation devices. The device may optionally be connected wirelessly to either or both of the physiological monitor and the stimulation device.

The device may be configured to receive and analyze information from the physiological monitor. The device may be configured to direct an electrical stimulation assembly to transmit output electrical stimulation (or another type of stimulation device to generate other stimulation). The output electrical stimulation may be epidural, for example. The device may cause the stimulation output to increase or decrease depending on the information received from the physiological monitor. The stimulation output may remain constant depending on the information received from the physiological monitor. The stimulation output may improve control of an autonomic function such as blood pressure. The device may operate by feedback control.

The device may be for use in a subject having dysregulated blood pressure. The dysregulated blood pressure may be due to SCI or other neurological conditions such as multiple sclerosis, autonomic failure, autonomic neuropathy, as well as cancer of the neurological tissue. The output electrical stimulation may raise or lower blood pressure in a subject with dysregulated blood pressure according to a set of predetermined parameters. The output electrical stimulation may be useful for controlling hypotension in a subject affected by dysregulated blood pressure.

Another aspect of the disclosure provides apparatus for controlling blood pressure in a subject. The apparatus comprises an input for receiving a BP signal indicative of a blood pressure measurement and a feedback control circuit connected to receive the BP signal from the input and to deliver a stimulation control signal to an output. The feedback control circuit is configured to: compare the blood pressure measurement to a target blood pressure range, if the comparison indicates that the blood pressure measurement is below the target blood pressure range increase a level of the stimulation control signal until the blood pressure measurement is in the target blood pressure range; and if the comparison indicates that the blood pressure measurement is above the target blood pressure range decrease a level of the stimulation control signal until the blood pressure measurement is in the target blood pressure range.

Another aspect of the disclosure provides a method for operating apparatus to control a subject's blood pressure. The method comprises: receiving at the apparatus a signal containing a blood pressure measurement indicative of the subject's blood pressure and comparing the blood pressure measurement to a predetermined target range stored in a data store accessible to the apparatus If the comparison indicates that the blood pressure measurement is below the target blood pressure range the method increases a level of a stimulation control signal until the blood pressure measurement is in the target blood pressure range. If the comparison indicates that the blood pressure measurement is above the target blood pressure range the method decreases the level of the stimulation control signal until the blood pressure measurement is in the target blood pressure range.

Another aspect of the disclosure provides apparatus for controlling one or more autonomous functions in a subject. The apparatus comprises: an input for receiving a monitor signal indicative of a parameter value and a feedback control circuit connected to receive the monitor signal from the input and to deliver a stimulation control signal to an output. The feedback control circuit is configured to: compare the parameter value to a target range. If the comparison indicates that the parameter value is below the target range the control circuit increases a level of the stimulation control signal until the parameter value is in the target range; and if the comparison indicates that the parameter value is above the target range the control circuit decreases a level of the stimulation control signal until the parameter value is in the target range.

Another aspect of the disclosure provides a method for operating apparatus to control one or more autonomous functions of a subject. The method comprises: receiving at the apparatus a signal containing a monitor measurement indicative of a parameter value; comparing the parameter value to a predetermined target range stored in a data store accessible to the apparatus; and, if the comparison indicates that the parameter value is below the target range increasing a level of a stimulation control signal until the parameter value is in the target parameter value range; and if the comparison indicates that the parameter value is above the target range decreasing the level of the stimulation control signal until the parameter value is in the target range.

Another aspect of the disclosure provides the use of any apparatus as described herein for controlling an autonomic function of a person affected by SCI.

Another aspect of the disclosure provides a method for medical treatment of subjects who have dysfunctional regulation of blood pressure or another autonomic function as a result of SCI (broadly interpreted as any condition which impairs operation of descending sympathetic pathways that normally facilitate control of autonomic functions). The method involves regulating the autonomic function by applying stimulation to structures in the lower back caudal to the SCI. The stimulation may comprise stimulating dorsal roots, dorsal afferent fibres and/or intraspinal structures that are connected directly or indirectly to sympathetic preganglionic neurons that affect the function being controlled.

The stimulation may be provided, for example, in the form of electrical stimulation. The electrical stimulation may be delivered to the dorsal aspect of the spinal cord of the subject, for example by way of an implanted electrode structure. The electrode structure is located caudal to the SCI, for example over the lumbosacral spinal cord segments (e.g. at T11-L1 vertebral levels). The method may involve feedback control of the stimulation based on monitoring a parameter that represents activity of the function being regulated. For example, the function may be blood pressure regulation and the parameter may be a blood pressure measured by a blood pressure monitor.

Further aspects of the disclosure and features and combinations of features of example embodiments are illustrated in the accompanying drawings and described below.

BRIEF DESCRIPTION OF THE DRAWINGS

The accompanying drawings illustrate non-limiting examples of the present technology.

DETAILED DESCRIPTION

Throughout the following description, specific details are given as examples in an attempt to impart a thorough understanding of the disclosure. However, the disclosure may be practiced in various forms not all of which embody such details. In other instances, well known elements have not been shown or described in detail to avoid unnecessarily obscuring the disclosure. Accordingly, the specification and drawings are to be regarded in an illustrative, rather than a restrictive sense.

One aspect of the present technology provides devices for automated control of a dysregulated autonomic function (such as blood pressure, bladder control and bowel control) in subjects. Such devices have particular application in treating subjects affected by SCI or other neurological conditions such as multiple sclerosis, autonomic failure, autonomic neuropathy, or cancer of the neurological tissue which impair operation of descending sympathetic pathways that normally facilitate control of autonomic functions.

Figure 1A:
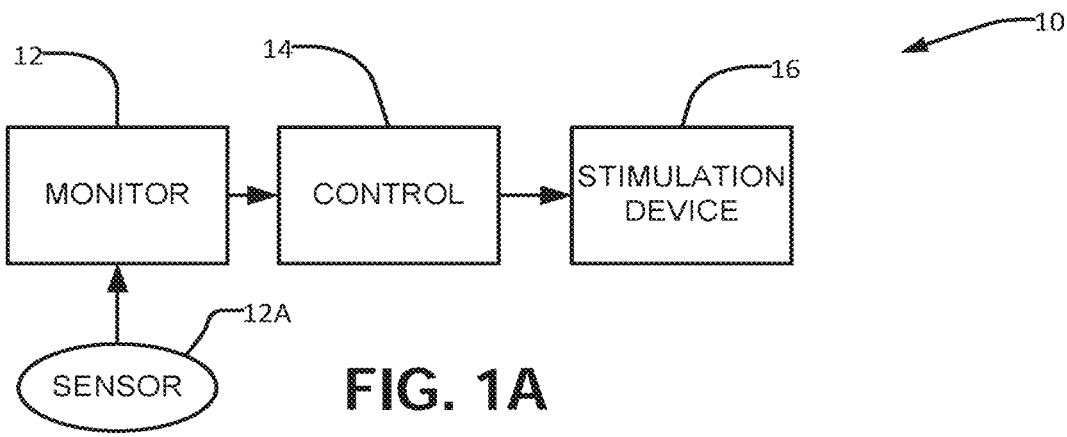
FIG. 1A is a block diagram illustrating an apparatus according to an example embodiment.

FIG. 1A illustrates an example apparatus 10 according to one embodiment. Apparatus 10 includes a monitor 12 which measures a parameter of an autonomic function of the subject. The parameter may, for example, comprise the subject's blood pressure, bladder volume, bladder pressure, etc. Monitor 12 includes a sensor 12A of a type suitable for the autonomic function being monitored. Sensor 12A may comprise a blood pressure sensor such as a cuff, an arterial pressure sensor, an optical biometric sensor etc. a bladder monitor such as a near infrared sensor (NIRS), an EMG sensor (such as a surface or needle type EMG sensor) for example. An EMG sensor may, for example, be located to measure activity of a muscle such as a muscle that controls the anal sphincter.

Control circuit 14 is configured to receive and analyze information from monitor 12. In the FIG. 1A embodiment control circuit 14 receives a signal indicating the parameter value from monitor 12. The information may comprise, for example, a parameter value such as a diastolic blood pressure, a systolic blood pressure, a diastolic blood pressure and a systolic blood pressure, a blended blood pressure value, a bladder volume, a bladder pressure, a measure of muscle tension or relaxation or the like. Control circuit 14 determines whether the measured parameter value is acceptable, too high or too low. In response to the determination, control circuit 14 controls a stimulation device 16 to apply stimulation to the patient.

The stimulation may be in any of one or more different forms. For example, the stimulation delivered by stimulation device 16 may comprise one or more of:
Electrical signals;
Optical signals;
Magnetic signals;
Optogenetic manipulation;
Chemogenetic manipulation;
Delivery of a chemical agent;
Thermal signals; etc.

In some cases the stimulation is delivered to the dorsal aspect of the spinal cord of a subject. The stimulation may affect dorsal roots, dorsal afferent fibres and/or intraspinal structures that are connected directly or indirectly to sympathetic preganglionic neurons that affect the function being controlled. The stimulation may be delivered caudal to a location of an SCI which has interrupted autonomic control of the function. While the inventors do not intend to be bound by any theory of operation, it is thought that stimulation delivered to affect dorsal roots, dorsal afferent fibres and/or intraspinal structures may be processed by neural structures in the spinal cord, particularly structures caudal to the SCI to cause signals on efferent nerves that, in turn, affect operation of the function being controlled.

Control circuit 14 may be integrated with monitor 12 and/or stimulation device 16 or may be provided as a stand-alone device that acts as an interface between monitor 12 and stimulation device 16. Where control circuit 14 is provided as a part of a stand-alone device, the device may comprise a specialized device or a programmed general purpose device such as a stand-alone CPU, microprocessor, mobile phone, tablet, etc.

The following sections provide more detailed example applications of the present technology to the control of blood pressure in subjects affected by SCI. It should be appreciated that all of these examples may be readily adapted for control of another function by replacement of a blood pressure monitor with a monitor that detects a parameter relevant to the function to be controlled and by suitable choice of stimulation. These examples describe electrical stimulation but may be adapted to use other types of stimulation by suitable choice of an alternative stimulation device.

Figure 1B:
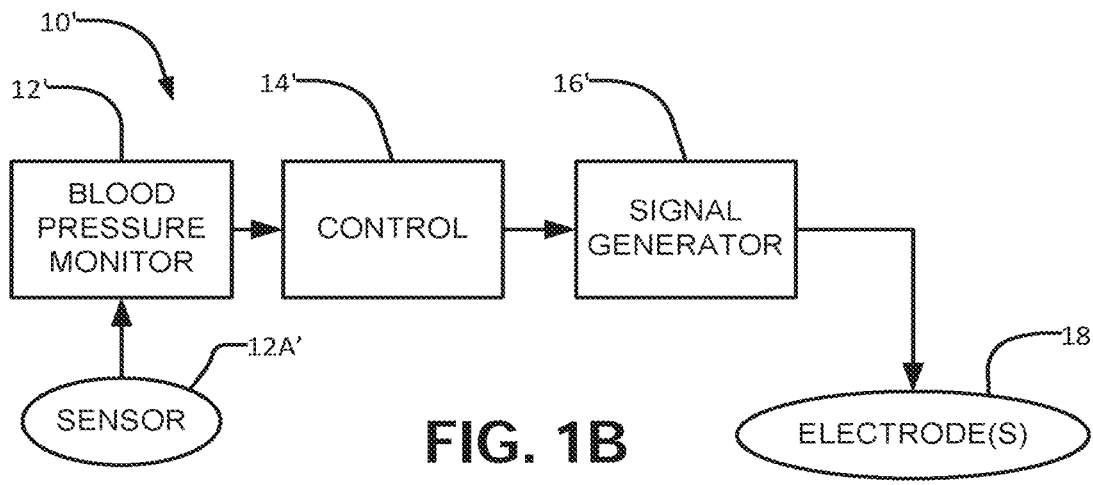
FIG. 1B is a schematic illustration showing a blood pressure control apparatus according to an example implementation.

FIG. 1B illustrates a more specific example apparatus 10'. Apparatus 10' is operable to control blood pressure of a subject. Apparatus 10' includes a blood pressure monitor 12' which measures the subject's blood pressure by way of a sensor 12A', a control circuit 14' which receives a signal indicating the subject's blood pressure from blood pressure monitor 12' and determines whether the blood pressure is acceptable, too high or too low.

Control circuit 14' is configured to receive and analyze information from blood pressure monitor 12'. The information may comprise, for example, a diastolic blood pressure, a systolic blood pressure, or a diastolic blood pressure and a systolic blood pressure. In response to the determination, control circuit 14' controls a stimulation circuit 16' to apply signals to the patient by way of electrode(s) 18.

Control circuit 14' may control any of a wide range of characteristics of electrical signals to be delivered by way of electrodes 18. For example, control circuit 14' may control one or any combination of: electrical stimulation voltage, the frequency of electrical stimulation, the pulse width of stimulation, the amplitude of stimulation, or any permutation of these factors or other electrical characteristics. The result is that apparatus 10' delivers electrical stimulation based on information received from the blood pressure monitor.

The signals delivered by control circuit 14 or 14' may, for example, comprise commands to be executed by a processor or other device in stimulation circuit 16' and/or parameters to be used by simulation circuit 16' in generating the stimulation and/or a waveform for stimulation signals in analog or digital form and/or a selection of a program to be used by stimulation circuit 16' in generating the stimulation.

Control circuit 14 or 14' may, for example, comprise one or any combination of: a programmed data processor (such as a microprocessor, industrial controller, embedded processor or the like), hardwired logic circuits and/or configurable logic circuits. Control circuit 14 comprises or has access to a data store or data registers which can contain parameters which affect control of the subject's blood pressure.

Embodiments of the disclosure including various designs for control circuit 14 or 14' may be implemented using any of:

- specifically designed hardware,
- configurable hardware,
- programmable data processors configured by the provision of software (which may optionally comprise "firmware") capable of executing on the data processors,
- special purpose computers or data processors that are specifically programmed, configured, or constructed to perform one or more steps in a method as explained in detail herein and/or
- combinations of two or more of these.

Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit 14 may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

Figure 1C:
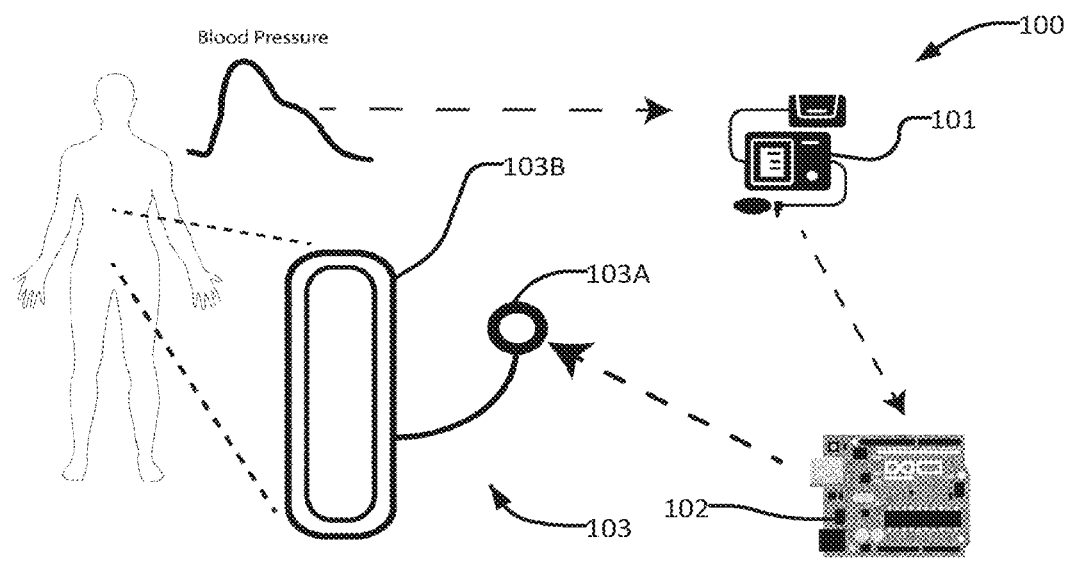
FIG. 1C is a schematic illustration showing a blood pressure control apparatus according to another example implementation.

FIG. 1C shows example apparatus 100 in which control circuit 14 is part of a device 102 that acts as an interface between a standalone blood pressure monitor 101 and an electrical stimulation assembly 103. Device 102 may, for example, comprise:

A processing unit
Circuitry which may comprise:
1. A receiving module
2. A transmitting module
3. A feedback control module
4. A memory for storing blood pressure and stimulation settings.

Figure 1D:
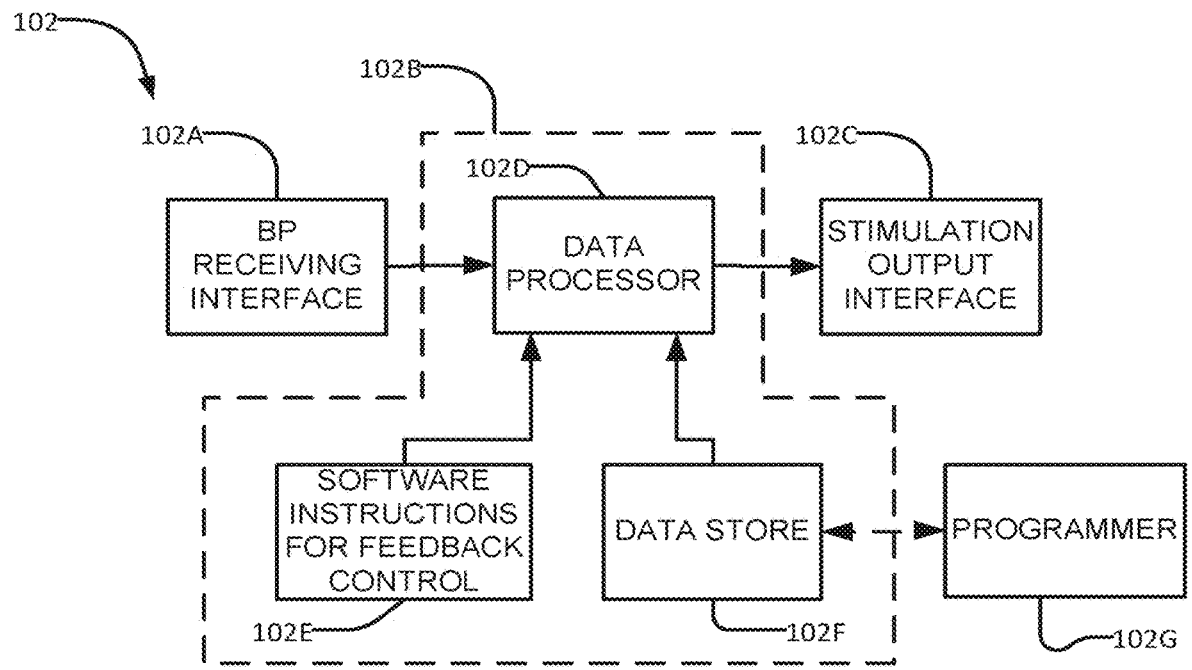
FIG. 1D is a block diagram of an example interface device.

FIG. 1D is a block diagram illustrating a possible construction for device 102. In this example, device 102 comprises a blood pressure receiving interface 102A, a feedback control circuit 102B and a stimulation output interface. Feedback control circuit 102B may have any of a wide variety of constructions. In this example, feedback control circuit 102B comprises a data processor 102D which executes instructions in a program store 102E. The instructions cause the processor to process blood pressure readings received by way of interface 102A and to determine stimulation settings. Parameters may be written to data store 102F, for example, by way of a programmer 102G or remote control/programmer that interfaces to device 102 by way of a wired or wireless data connection. Parameters stored in a data store 102F may be applied in determination of the stimulation settings. The stimulation settings are output to a stimulation system by way of interface 102C.

Device 102 may interface with blood pressure monitor 101 and electrical stimulation assembly 103 in any suitable manner including wirelessly. Interfaces 102A and 102C may, for example, comprise:

- wireless data interfaces such as WiFi, Bluetooth, or the like;
- wired or optical data interfaces.

In some embodiments both of interfaces 102A and 102C are provided by the same physical hardware.

Blood pressure monitor 101 may comprise any blood pressure measuring device. For example, blood pressure monitor 101 may be provided by any of:

- a beat-by-beat finometer device.
- a device that operates by discrete brachial auscultation methods,
- a wrist watch with blood pressure measurement circuitry,
- a phothoplethymography device,
- a tonometer,
- an intra-arterial blood pressure measuring cannula.

Electrical stimulation assembly 103 may be provided by any suitable stimulation assembly capable of providing spinal cord electrical stimulation as described herein. For example, electrical stimulation assembly 103 may comprise a commercially-available electrical stimulation device. The electrical stimulation assembly may, for example, provide epidural spinal cord stimulation.

The electrical stimulation assembly may comprise one or more stimulation electrodes 103B connected to an electrical pulse generator 103A. In some embodiments electrodes 130B are provided on an implantable device. The implantable device may, for example, comprise a commercially available electrode paddle. A wide range of suitable implantable electrode structures are commercially available. These electrode structures differ in the number of electrodes provided (configurations which include 8, 16, or 32 electrodes and associated contact leads are common). Such structures may be designed for surgical or percutaneous application and are dimensioned to fit within the dimensions of the spinal canal at the appropriate spinal segment.

Device 102 may be programmed to decide, based on pre-determined criteria, the appropriate stimulation output to be supplied by electrical stimulation assembly 103. The criteria may, for example, include one or more of:

- one or more parameters that indicate what blood pressure is desirable for a subject;
- one or more parameters that indicate how the subject responds to stimulation from electrical stimulation assembly 103;
- one or more parameters that specify characteristics of a stimulation signal (e.g. frequency, current, pulse width, pulse repetition frequency, for an electrical stimulation signal);

one or more parameters that affect operation of an algorithm or method executed by device 102 (e.g. an amount to increment a stimulation level when it is desired to increase blood pressure, an amount to decrement a stimulation level when it is desired to decrease blood pressure, a lag time to wait before further adjusting the stimulation level etc.).

The appropriate stimulation output may, for example, be based on a predetermined target blood pressure range for an individual. The target blood pressure range may, for example, be predetermined by a medical professional (e.g. a physician, pharmacist, physician-aid or other trained operator). The target blood pressure range may be predetermined based on the resting blood pressure of the subject prior to stimulation, and/or other criteria as determined by a medical professional. In some embodiments the target blood pressure range is adjustable based upon a user input that allows a medical professional and/or the subject to move the target blood pressure range toward higher or lower blood pressures. The user input may be provided for example using programmer 102G or some other interface that is connected to control device 102.

The appropriate stimulation output may also be based on the comfort and/or safety of the subject. For example, the stimulation output may be selected so that a stimulation level is kept lower than a threshold above which the stimulation becomes uncomfortable to the subject and/or causes side effects such as spasticity.

The appropriate stimulation output may optionally be based on a mode of operation of device 102. For example, device 102 may have a plurality of routines where each routine may specify different parameters. For example, a "Morning sit up stimulation routine" may control for a higher blood pressure than an "afternoon resting routine". In some embodiments a subject may select among the plurality of routines using programmer 102G or some other interface that is connected to control device 102. In some embodiments, device 102 incorporates a scheduler that automatically selects one of a plurality of routines based on time of day.

The appropriate stimulation output may be expressed as characteristics of one or more electrical stimulation signals to be delivered to the subject. These characteristics may, for example, comprise:

an amplitude (e.g. voltage and/or current) of the signal(s),
an electrical pulse frequency of the signal(s),
a pulse width of stimulation,
a polarity of the stimulation,
a selection of electrodes for delivery of the stimulation,
other electrical characteristics of the signal(s); or
any combination/permutation of these factors.

Figure 2A:
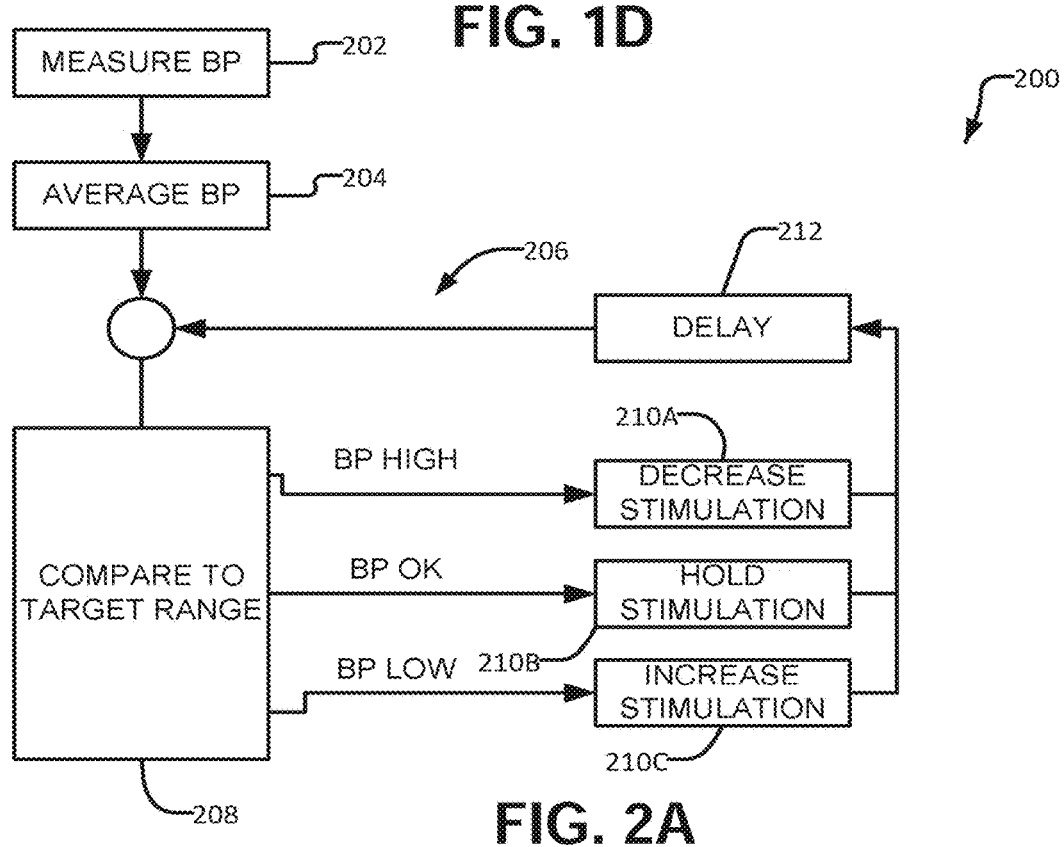
FIG. 2A is a flow chart showing an example method for operating an apparatus to control an autonomic function of a subject such as the subject's blood pressure.

FIG. 2A illustrates an example feedback control/decision making algorithm 200 that may be used in accordance with the present disclosure. Such an algorithm may, for example, be implemented using software instructions 102E. Block 202 receives a stream of blood pressure measurements. For example, blood pressure measurements may be received on the order of a few to a few tens of measurements per minute. Block 204 determines a running average blood pressure that is made available to the rest of method 200. Block 204 may, for example, determine an average blood pressure for an immediately previous period. For example, the average may be determined for a period having a length of a few seconds to a few minutes (e.g. 30 seconds).

Method 200 includes loop 206 which begins by comparing at 208 the current average blood pressure from block 204 to the target range. If the presently measured average blood pressure exceeds the target range then block 210A triggers a reduction of the stimulation level. If the presently measured average blood pressure is within the target range then block 210B holds the stimulation at the current level. If the presently measured average blood pressure is below the target range then block 210C triggers an increase of the stimulation level. Block 212 delays for a short period before the next iteration of loop 206.

An increase or reduction of the stimulation level may be achieved by incrementally increasing or reducing the stimulation level. The increments may be predetermined fixed increments or may be set based on factors such as how far away from the target range is the presently measured blood pressure. In an example embodiment the increment size is increased in proportion to a difference between the presently measured blood pressure and the closest part of the target blood pressure range. Increments for increasing and decreasing the stimulation level may be the same or different. Another way to increase or reduce the stimulation level comprises ramping the stimulation level up or down. The rate(s) at which the stimulation level are ramped up or down may be fixed or variable. In some embodiments the rates of increase and/or decrease are set as a function of a difference between the presently measured blood pressure and the closest part of the target blood pressure range. The rates of increase and/or decrease may be higher when a difference between the presently measured blood pressure and the closest part of the target blood pressure range is larger.

Figure 2B:
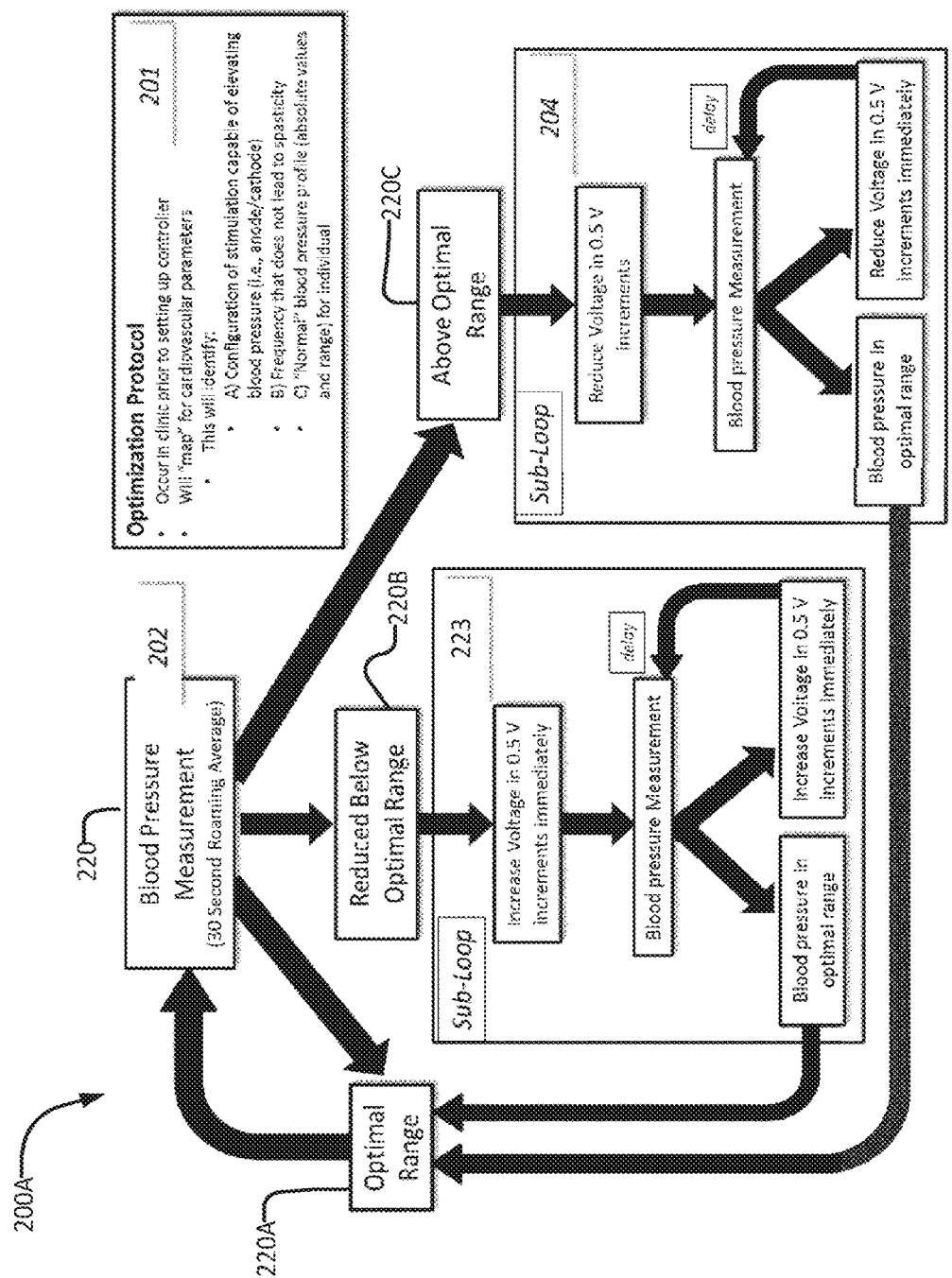
FIG. 2B is a flow chart illustrating another example control mechanism with feedback loops to be engaged when blood pressure is either above or below a predetermined target range.

FIG. 2B shows another example of a blood pressure feedback control algorithm 200A that may be executed by a device 102 and/or a feedback circuit 14. Control algorithm 200A may detect whether the measured blood pressure of a subject (220) is within the target range (block 220A) or outside of the target range. If the measured blood pressure of a subject is below the predetermined target range (block 220B) then sub-loop 223 is engaged. In sub-loop 223 the stimulation level supplied by stimulation apparatus 103 is elevated. This may be done, for example, by increasing a voltage and/or current of an electrical stimulation signal and/or by adjusting a frequency of the electrical stimulation signal to a frequency that is more effective for increasing blood pressure. For example, the stimulation voltage or current may be increased incrementally by performing sub-loop 223 until the target blood pressure range is reached.

In some embodiments the stimulation voltage is elevated in increments having sizes in the range of 0.1 V-10 V. The stimulation assembly may be configured, for example, to elevate voltage in 0.5 V increments. The voltage may be elevated incrementally. The voltage increments may be predetermined by a medical professional. The voltage increments may be determined on a per subject basis.

The increments may be selected depending on the type of stimulation assembly used. For example, where an epidural stimulation assembly is used, the electrical stimulation may be elevated in increments in the range of about 0.1V to 30 V (or about 0.4V to about 2.5V). As another example, where a transdermal stimulation assembly is used, the electrical stimulation may be increased by delivering higher currents. For example, electrical current may be elevated in increments in the range of about 0.1 to about 150 mA (in some embodiments, the increments of electrical current are about 20 mA).

If blood pressure does not elevate into the target range in response to an incremental increase in stimulation level, then sub-loop 223 may further increase stimulation voltage at the predetermined increment until a blood pressure within the target blood pressure range is reached or until a maximum stimulation level has been reached. As mentioned above, the maximum stimulation level may be set to preserve the subject's comfort and/or safety.

In some embodiments method 200 stops increases in stimulation level in response to receiving a "STOP" command. The stop command may be issued in response to the subject activating a button or other control, for example.

Blood pressure may not respond instantaneously to excitation of sympathetic preganglionic neurons, and therefore there may be a lag between commanding a change in a stimulation level and a consequential change in the subject's blood pressure. For this reason, method 200 provides a lag duration between a time when a stimulation level is set and a next time at which the stimulation level adjustment. This lag may be on the order of seconds, for example. In some embodiments the lag is at least 10 seconds. The device can operate with a variety of lag durations from 1 second to an hour or more on a per subject basis. For example, the device provides a lag duration in the range of a few seconds to 15 minutes. In some embodiments, the device provides a lag duration of about 10 seconds.

In some embodiments the lag is variable. For example, the lag may be reduced in cases where the presently measured blood pressure is far from the target range and the lag may be increased in cases where the presently measured blood pressure is close to or within the target range.

If a blood pressure within the target range is reached (block 220A), the stimulation level may be maintained until blood pressure deviates from the target range.

If blood pressure is above the upper threshold of the predetermined target range (block 220C) then sub-loop 224 is performed to reduce blood pressure by reducing the stimulation level supplied by stimulation system 103. For example, stimulation voltage and/or current may be reduced. In this manner the stimulation level may be reduced until a blood pressure within the target blood pressure range is reached.

The reduction may be incremental. For example, voltage and/or current increments may be predetermined by a medical professional and may be the same as or different from the increment used in sub loop 223. The increments may be determined on a per subject basis. Stimulation voltage may be reduced in increments in the range of 0.1 V-10 V for example. In some embodiments, stimulation assembly 103 reduces voltage in increments of about 0.5 V each time sub-loop 224 is executed. If a blood pressure within the target range is reached (block 220A), the stimulation intensity may be maintained until blood pressure deviates from the target range.

The stimulation increments may vary depending on the type of stimulation assembly used. For example, where a transdermal stimulation assembly is used, the electrical stimulation may be decreased in increments in the range of about 0.1 mA to about 150 mA (or about 20 mA). Where an epidural stimulation assembly is used, the electrical stimulation may be decreased in increments in the range of about 0.1V to about 30V (or about 0.3V to 2.4V, for example 2V, or about 0.5V).

If blood pressure does not decrease sufficiently in response to an incremental decrease in voltage by sub-loop 224, then stimulation voltage may be further decreased by the predetermined increment until a blood pressure within the target blood pressure range is reached.

Blood pressure may not respond instantaneously to the reduction of excitation of sympathetic preganglionic neurons, and therefore there may be a lag of at least 10 seconds between stimulation and the subsequent blood pressure detection and voltage adjustment. The device can operate with a variety of lag durations from 1 second to several hours on a per subject basis. For instance, the device can operate with a lag duration from a few seconds to 15 minutes. In some embodiments, the device operates with a lag duration of less than about 1 minute, such as a lag duration of about 10 seconds.

In some embodiments, the stimulation output has one or any combination of two or more of the following characteristics:

the stimulation output comprises electrical pulses presented at a pulse frequency in the range of about 5 Hz to 10 kHz (or about 30 Hz to about 60 Hz);

the stimulation output comprises electrical pulses having a pulse width in the range of about 0.002 seconds to about 20 seconds (or about 0.033 seconds to about 0.17 seconds);

the stimulation output has a voltage in the range of about 0.1 V to about 24 V;

the stimulation output has a voltage in the range of about 0.1 V to about 500 V;

3a the stimulation output has an amperage in the range of about 0 mA to about 1000 mA.

In some embodiments where the stimulation signals are delivered by way of an epidural stimulator the stimulation output has a voltage in the range of about 0.1 V to about 20 V and an amperage in the range of about 0 mA to about 100 mA.

In some embodiments where the stimulation signals are delivered by way of a transcutaneous stimulator the stimulation output has a voltage in the range of about 0.1 V to about 100 V and an amperage in the range of about 0 mA to about 100 mA.

In accordance with one aspect of the disclosure, the device may be used to control blood pressure in a subject with dysregulated blood pressure. The dysregulated blood pressure may be due to SCI or other neurological conditions including, but not limited to, multiple sclerosis, autonomic failure, autonomic neuropathy, as well as cancer of the neurological tissue. The device may be used to control blood pressure in a subject with SCI. In one aspect of the disclosure, the device may control electrical stimulation of the spinal cord. Electrical stimulation of the spinal cord may be performed caudal to injury. Electrical stimulation of the spinal cord may be performed at spinal segments T1-L1, as well as anywhere over the thoracic segment where sympathetic preganglionic neurons are stimulated to elicit a blood pressure effect.

Methods and apparatus as described herein may be applied in combination with pharmacological agents that affect blood pressure. For example, methods and apparatus as described herein may be applied to a subject who is being treated with a pharmacological agent for increasing blood pressure. The use of the present apparatus and methods may reduce the dosage of the pharmacological agent required and/or the time between doses of the pharmacological agent. This may reduce side effects of the pharmacological agent in some cases. Further, use of the present apparatus and methods may maintain control over blood pressure during the time required for a dose of the pharmacological agent to take effect.

The present disclosure may be applied to control autonomic functions other than blood pressure. For example, apparatus and control algorithms as described herein may be applied for controlling a variety of autonomic processes in a subject using electrical or other stimulation. Autonomic processes may include regulation of blood pressure, bladder/bowel control, sexual function, etc.

A device comprising a circuit 14 as described herein may receive input from any of a variety of physiological monitors and control a variety of electrical stimulation assemblies in response to the inputs. Such a device may be configured to receive information from the physiological monitor, and analyze such information based on a control algorithm as described above for example. The device may be configured to direct the electrical stimulation assembly to transmit output electrical stimulation based on the control algorithm. The output electrical stimulation may be transdermal or epidural. In some embodiments, epidural delivery of electrical stimulation is used. The stimulation output may increase or decrease depending on the information received from the physiological monitor. The stimulation output may remain constant depending on the information received from the physiological monitor. The stimulation output may improve control of any of a range of autonomic functions. The control interface may operate by feedback control.

For example, epidural spinal cord stimulation as described may be applied to acutely modulate bladder and/or bowel function in subjects affected by SCI. This may be done by providing a program to deliver stimulation that facilitates urination and/or bowel function and providing an interface that allows a subject to input a command to perform the program. The program may specify a type of stimulation that is specific to bladder/bowel control and that does not significantly affect blood pressure or other functions. A device as described herein may be configured to temporarily suspend active control over BP while performing a bowel/bladder control program and/or the bladder/bowel control program may be performed in parallel with control of blood pressure or other autonomous functions as described herein.

For example, in an example case a program that involved applying electrical stimulation comprising a pulse width 450 ms, a frequency of 45 Hz, and an intensity of 6V for a stimulation time of 105 s led to an increase in external anal sphincter/pelvic floor muscle tone (as measured by EMG) and detrusor pressure (Pdet). This stimulation was found to reduce the time required for bowel evacuation from 117 to 23 minutes (i.e. >80%). The stimulation was applied using a subset of the electrodes provided by an implanted 16-electrode array (Specify 5-6-5, Medtronic, Minneapolis, MN, USA) placed at the T11-L1 vertebral levels and driven by a neurostimulator (RestoreAdvanced SureScan™ MRI neurostimulator). The subset of electrodes was selected to affect bladder/bowel function.

Figure 8A:
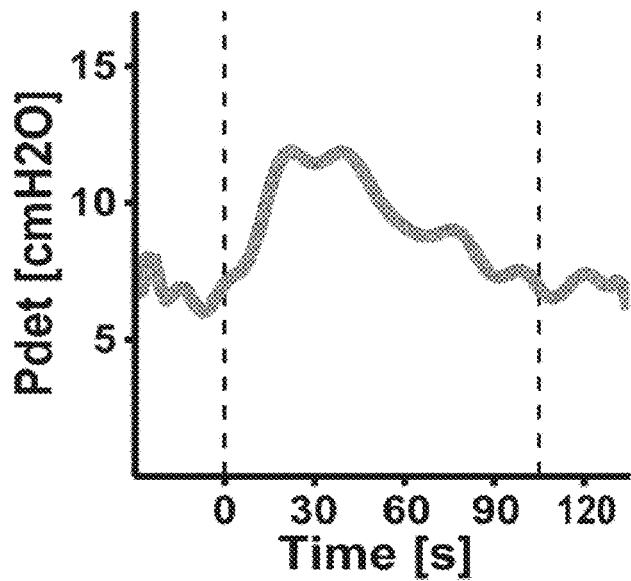
FIGS. 8A, 8B, and 8C are graphs respectively illustrating the effect of stimulation to control bladder/bowel function on detrusor pressure (Pdet), floor muscle tone (EMG) and blood pressure (BP)/heart rate (HR).
Figure 8B:
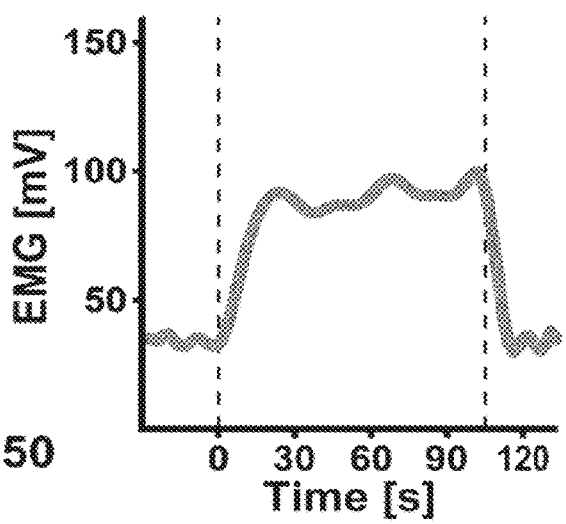
Figure 8C:
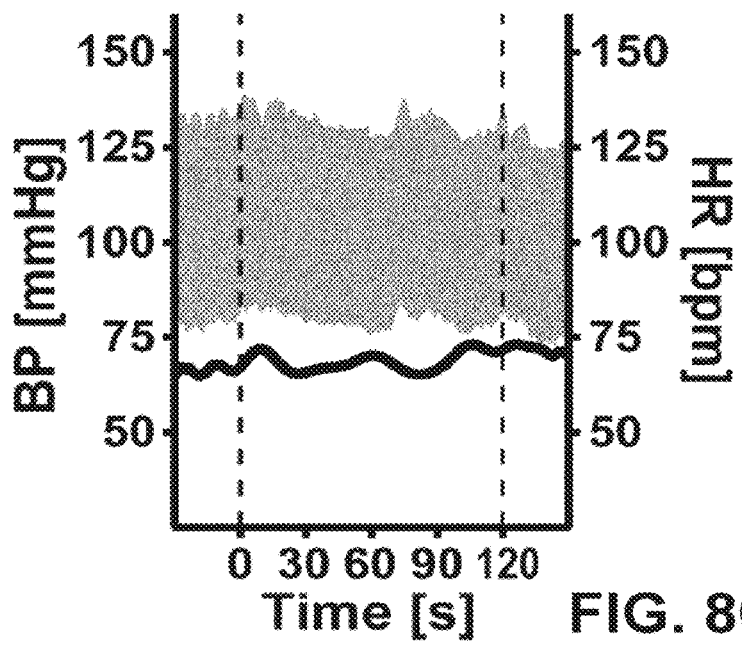

FIGS. 8A to 8C show that the stimulation led to an increase in external anal sphincter/pelvic floor muscle tone (EMG) and detrusor pressure (Pdet). Blood pressure (BP) and heart rate (HR) remained stable during stimulation. Dashed lines indicate start and stop of stimulation.

In some embodiments blood pressure monitor 101 is replaced with a monitor for measuring urinary bladder/bowel volume. In such embodiments a measured bladder volume may be processed to alter signals delivered to control bowel/bladder function.

Without committing to any particular theory of operation, it is thought that stimulation delivered by way of such electrodes may activate sympathetic and/or parasympathetic spinal neuronal structures in the lower part of the spinal cord to cause changes of functions in blood vessels, bladder, bowel and/or sexual organs. The neuronal structures involved may be located within the T11 to S5 segments of the spinal cord, for example. Stimulation may be configured to control a particular function by selecting electrodes and/or the nature of the stimulation.

The desired structures may be stimulated transdermally. Transdermal stimulation may incidentally also activate afferent fibres in skin/underlying tissue.

Blood pressure or another function may be controlled by electronic feedback control. This may be done by monitoring one or more parameters that indicate activity of the function being controlled and setting a level of the stimulation based on the monitored parameters. In the case of blood pressure the monitored function may be blood pressure itself (measured using any available blood pressure monitoring modality). The stimulation level may be controlled to keep blood pressure within a target range. Such stimulation may be particularly useful for raising blood pressure to counteract the extreme hypotension that often accompanies SCI.

In some embodiments the method involves administering to the subject pharmacological agents that have the effect of raising blood pressure and adjusting the stimulation level automatically to maintain the desired blood pressure taking into account the effect of the pharmacological agent. This control may cause the stimulation level to be higher in the period before the pharmacological agent takes full effect. The stimulation level may be lower (or off) when the pharmacological agent is fully effective. The stimulation level may then increase as the pharmacological agent is metabolized or excreted or otherwise ceases to maintain blood pressure.

In some embodiments the method may comprise selection of a program for control of an autonomic function. Different programs may be provided for the same autonomic function. Different programs may differ, for example, in one or more of:

Target level for the function (e.g. target blood pressure range);
Lag time for control (e.g. time constant for feedback);
Rate of increase or decrease of stimulation level;
Maximum allowed stimulation level etc.

A program may be selected from among a plurality of programs in response to user input by way of a suitable control, an automatic scheduler and/or the like. Where the stimulation is delivered by way of apparatus as described herein, programs may be defined by stored data which may be resident in a control circuit (e.g. 102) or a stimulator (e.g. 103) or a device which combines these functions, for example.

In some embodiments, the method may include control of plural autonomic functions. For example, the method may involve controlling blood pressure and also controlling bladder/bowel function. In such cases, different stimulation may be provided for each of the autonomic functions. The stimulation for the different functions may be selected in such a manner that the stimulation associated with one function does not significantly affect another function. This may be achieved, for example, in the case of electrical stimulation, by one or more of:

using different combinations of electrodes for stimulation of the different functions;
using different polarities of stimulation;
using different frequencies, waveforms or other stimulation signal characteristics for the different functions etc.

Control of the bladder/bowel function may be applied selectively to assist a subject with urination and/or bowel voiding. Where this is done in combination with control over blood pressure the stimulation for blood pressure control may be performed concurrently with stimulation of bowel/bladder function or the stimulation for blood pressure control may be temporarily interrupted while applying stimulation for bowel/bladder function.

Stimulation for sexual function may be handled in the same or a similar way to stimulation for bowel/bladder function.

EXAMPLES

Prototype embodiments of systems as described herein have been tested on a number of subjects in a study that was approved by the clinical research ethics board of the University of Louisville, the University of California Los Angeles, and the University of British Columbia. Each of the subjects presented with motor, sensory, and autonomic completeness of injury. Each of the subjects provided written informed consent. All subjects of the study were:
- screened for the presence of orthostatic intolerance and exhibited a reduction in systolic arterial blood pressure of at least 20 mmHg in response to a sit-up test;
- assessed for neurological level and completeness of injury according to standard guidelines.

Epidural Electrical Spinal Stimulation

An epidural spinal cord stimulation unit (RestoreADVANCED™, Medtronic, Minneapolis, MN, USA) in combination with a 16-electrode array paddle 301 (see FIGS. 3A to 3G). Paddle 301 was a 5-6-5 paddle from, Medtronic, Minneapolis, MN, USA. Paddle 301 was implanted at T11-L1 vertebral levels over the lumbosacral spinal cord segments. 1 During the implantation surgery, the electrode array was positioned over the midline of the exposed dura and its location was assessed intraoperatively with thresholds and amplitudes of electromyography (EMG) recorded from leg muscles elicited by stimulation at 2 Hz. Two wide-field stimulation configurations, where the anodes where located at the most rostral three locations on the electrode, and the cathodes were located at the most caudal three portions of the electrode, (or vice versa) were used for stimulating and eliciting these effects.

General Integrated Hemodynamic Assessment Approach

At least one month after implantation surgery, and following the development of a cardiovascular optimized stimulation paradigm (CV-scES); i.e., elucidating the optimum stimulation parameters that could modulate blood pressure) as shown at 201, we conducted a within person trial to investigate the immediate cardiovascular effects of CV-scES. The three participants were randomized to receive either stim-on or stim-off condition first and the two testing sessions were separated by no more than 24 hours.

Figure 3A:
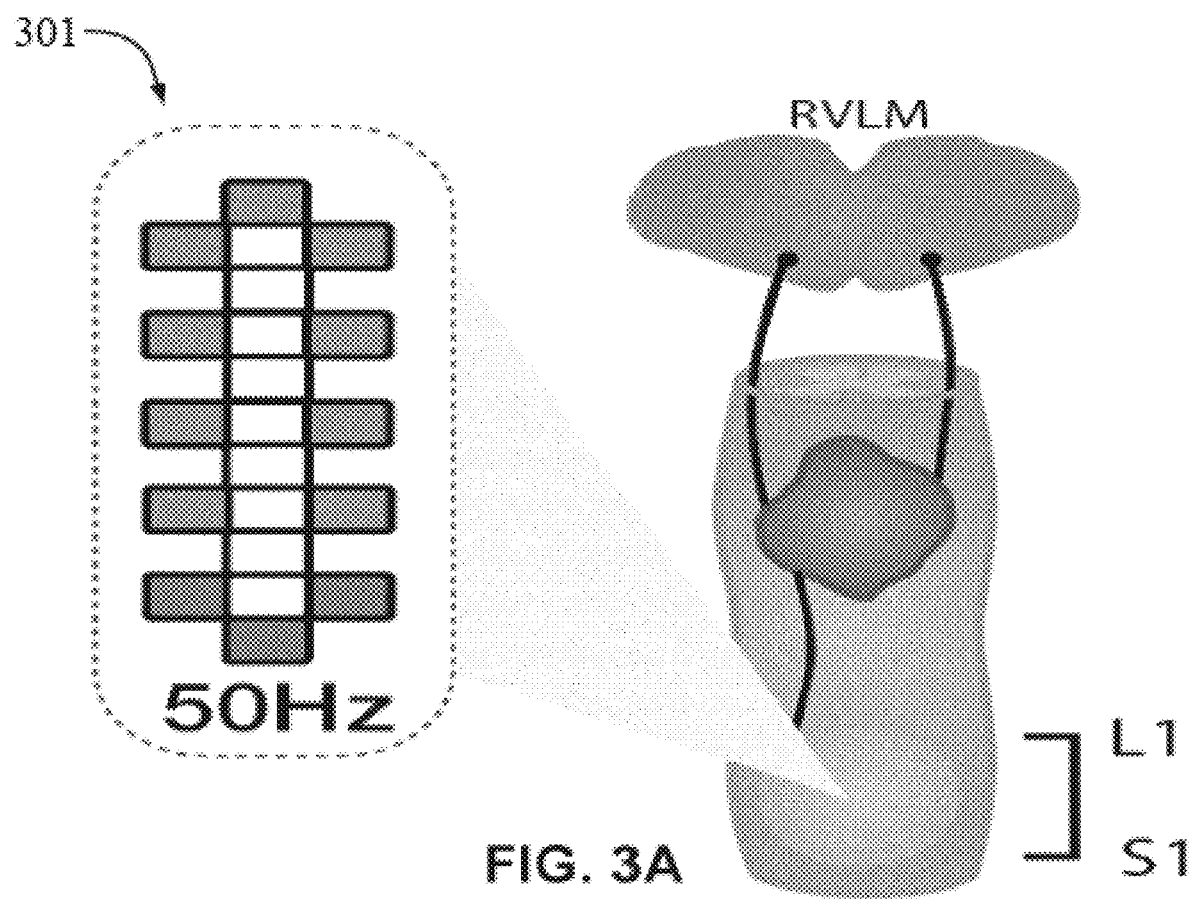
FIGS. 3A to 3G illustrate the restoration of cardiovascular control in individuals with SCI in response to controlled electrical spinal cord stimulation.
Figure 4A:
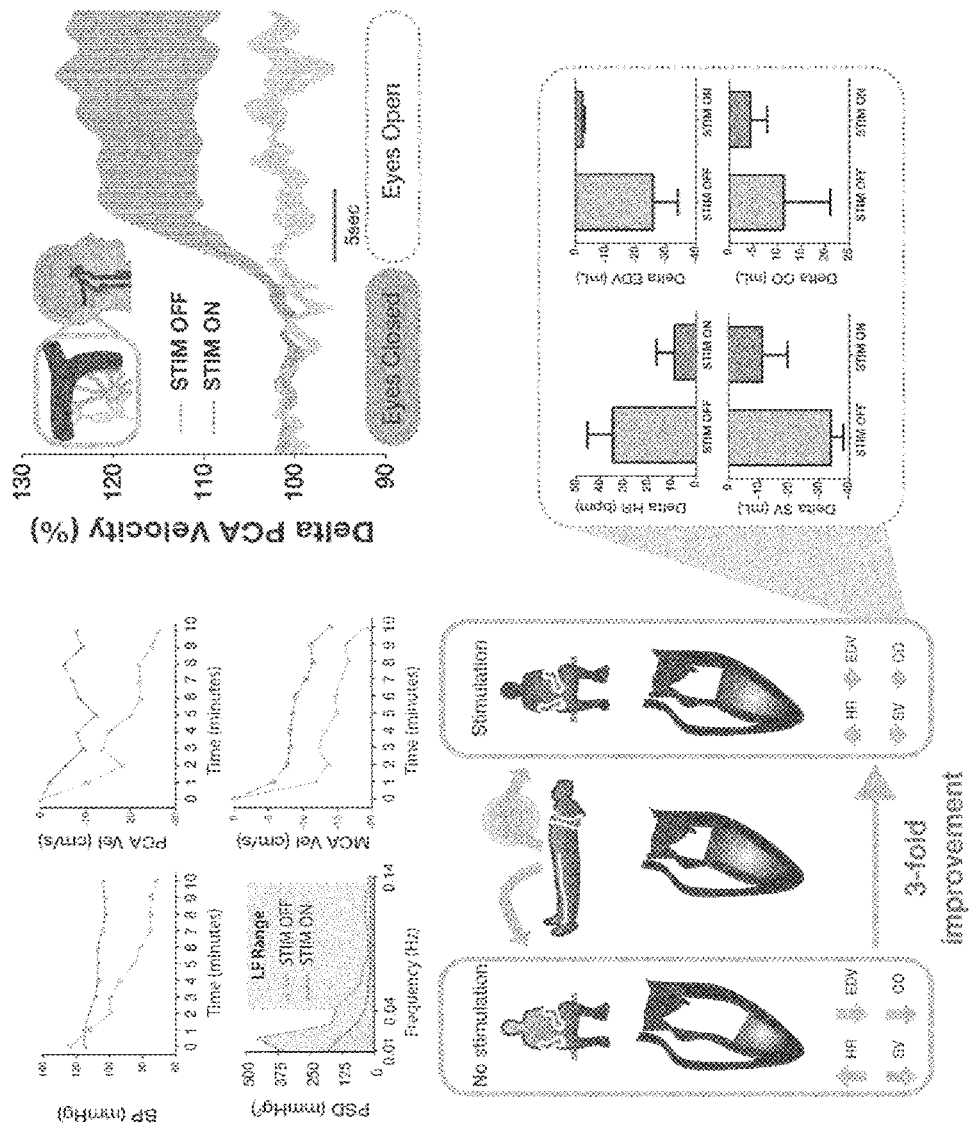
FIGS. 4A to 4D illustrate improved cardiovascular function in individuals with SCI that received optimized epidural spinal stimulation.
Figure 4B:
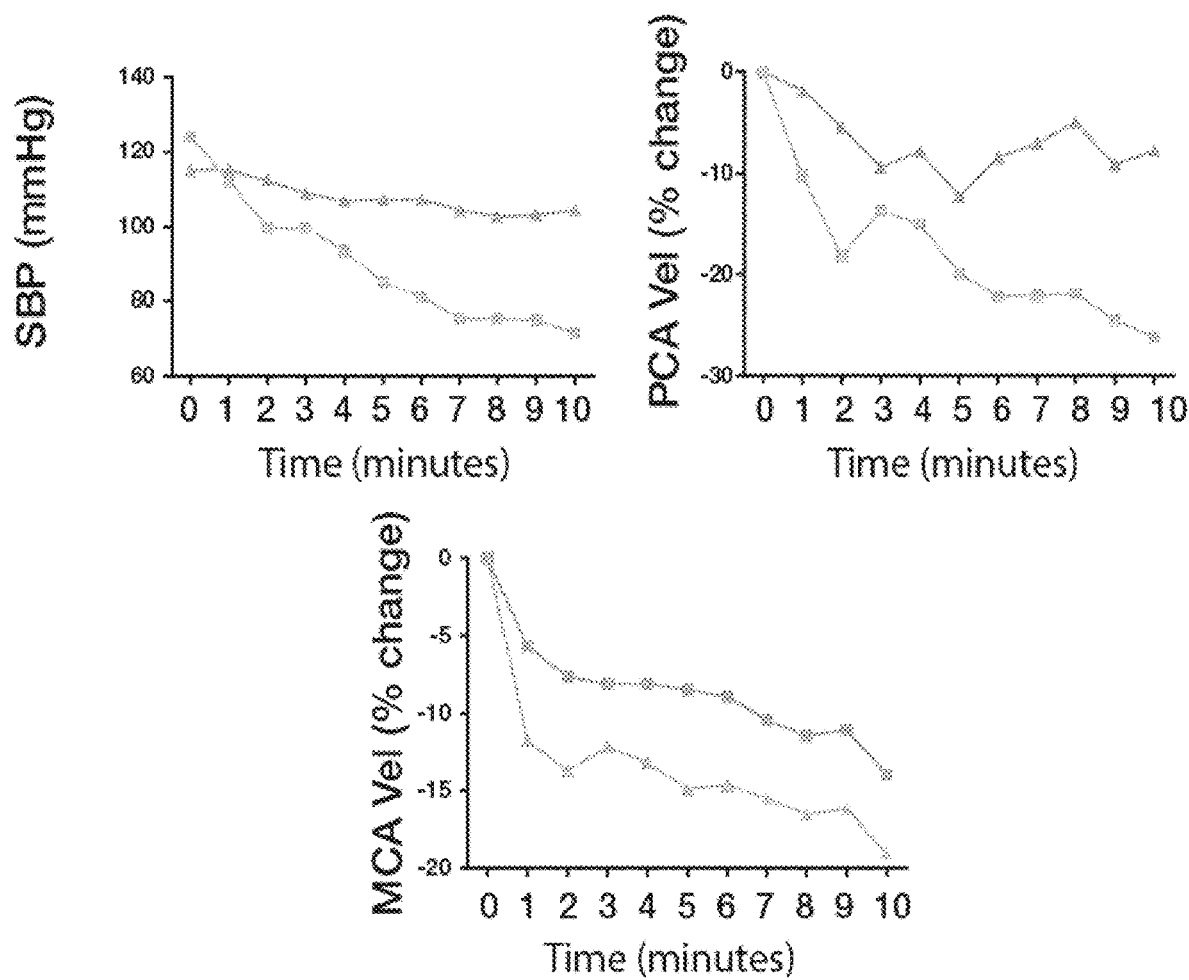
Figure 4C:
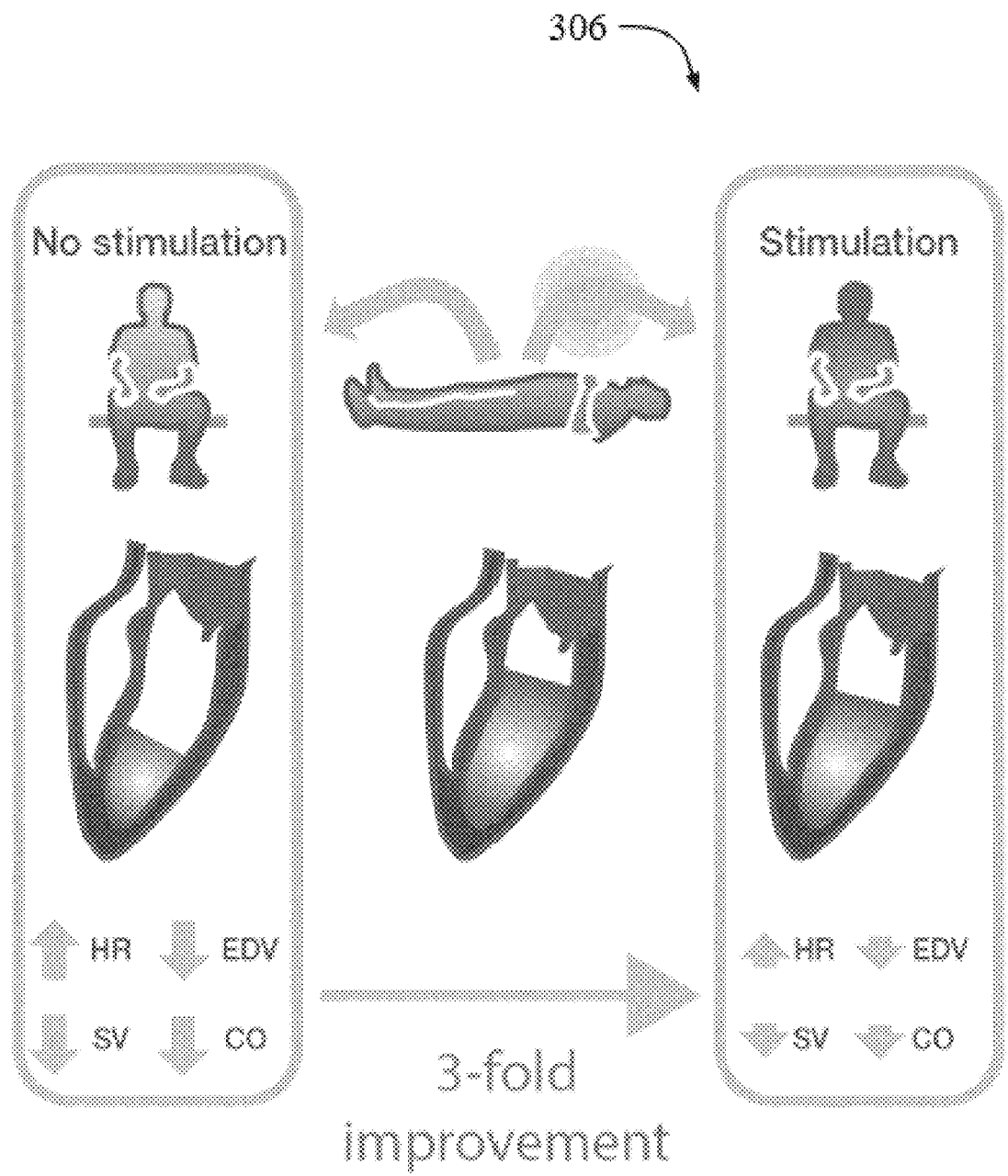

FIG. 3A includes beat-by-beat blood pressure via finger photoplethysmography (Finometer PRO™, Finapres Medicine Systems, Amsterdam, Netherlands) corrected to brachial pressure (Dinamap, General Electric Pro 300V2; Tampa, Florida, USA), electrocardiogram, central sympathetic outflow via sympathetic skin responses, cardiac function via echocardiography (Phillips EPIQ7™, Philips Medical System, Andover, MA, USA), and neurovascular coupling by insonating the middle and posterior cerebral arteries with a transcranial Doppler (ST3 Transcranial Doppler™, Spencer Technologies, Redmond, WA, USA). During the sit-up position only, we also assessed executive function (i.e., verbal fluency), as well as attention/concentration (Stroop test; FIGS. 4A and 4C Part 306). All procedures were assessed in the supine position and then in response to sit-up with and without stimulation.

Figure 3B:
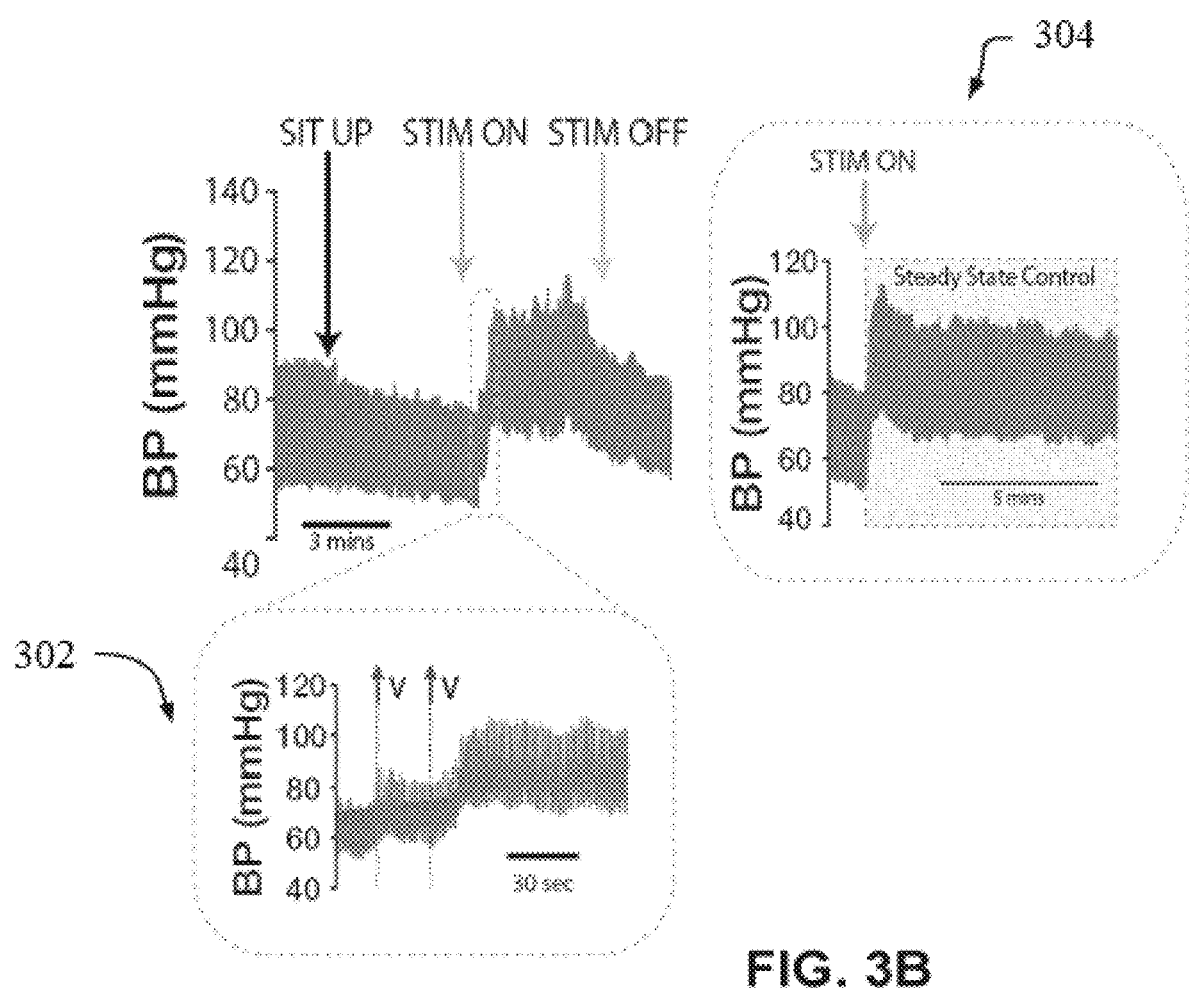

Example 1: Restoration of Integrated Cardiovascular Control in Response to Epidural Stimulation FIG. 3A illustrates the cardiovascular response of an individual following controlled electrical stimulation. All panels show raw cardiovascular data for one study participant. Parts 304 and 302 in FIG. 3B show the participant's acute blood pressure responses to increases and decreases in voltage where blood pressure is accurately controlled and regulated by titration of stimulation up and down, and subsequent increases in voltage lead to further increase in blood pressure. Part 302 shows that acute reductions in voltage can reduce blood pressure in a controlled and incremental way.

Raw blood pressure traces 302 indicate that when the stimulator was activated there was an immediate reversal of orthostatic hypotension that was achieved in a controlled manner by gradually increasing voltage. Orthostatic hypotension prevailed again when the stimulator was turned off, demonstrating a capability to dynamically modulate blood pressure. Under steady state conditions, the stimulator was able to offset chronic hypotension by increasing and maintaining blood pressure approximately 20 mmHg above resting baseline, and increased low-frequency oscillations in systolic blood pressure indicating a return of medullary cardiovascular control.

Figure 3C:
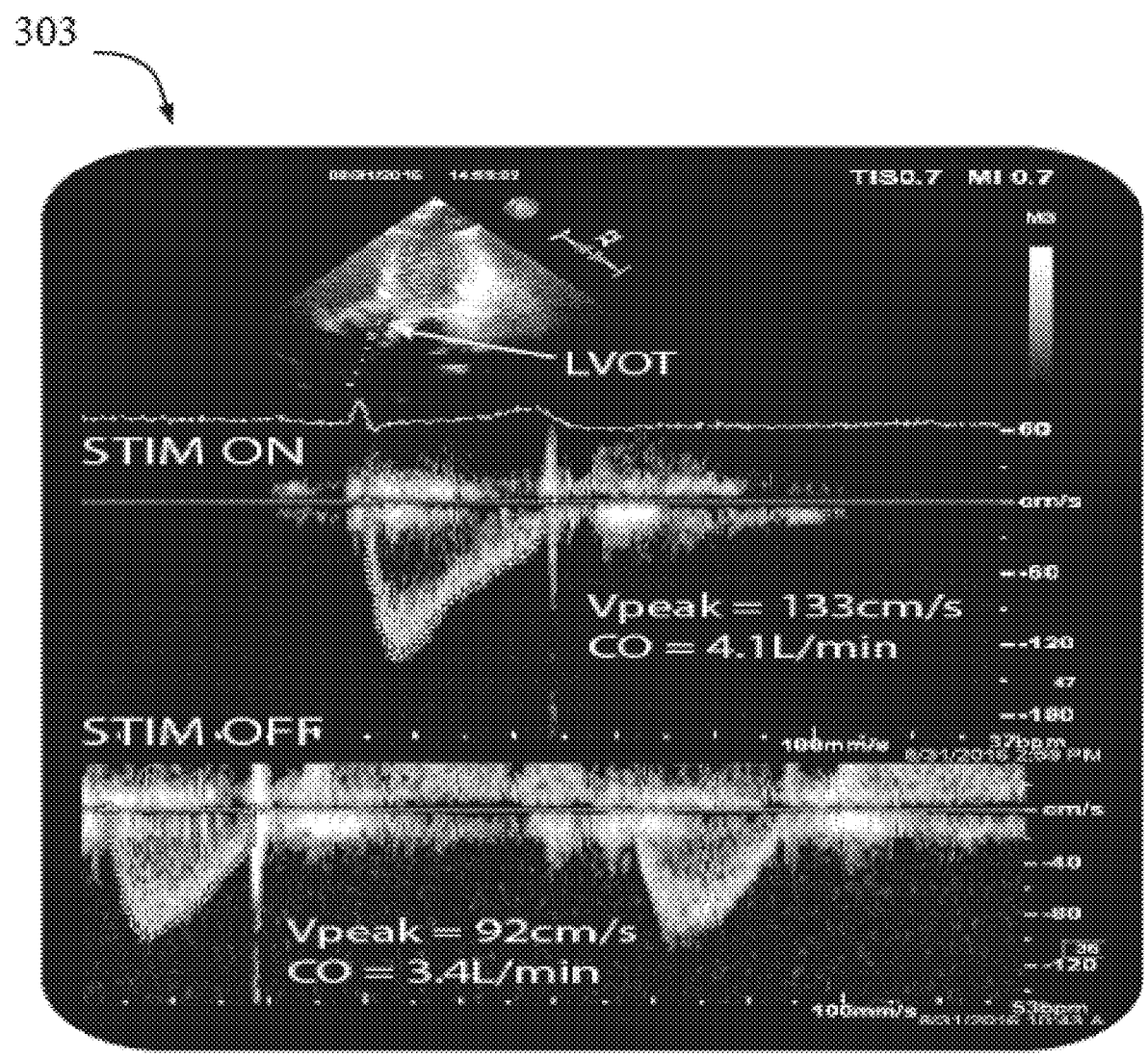
Figure 3D:
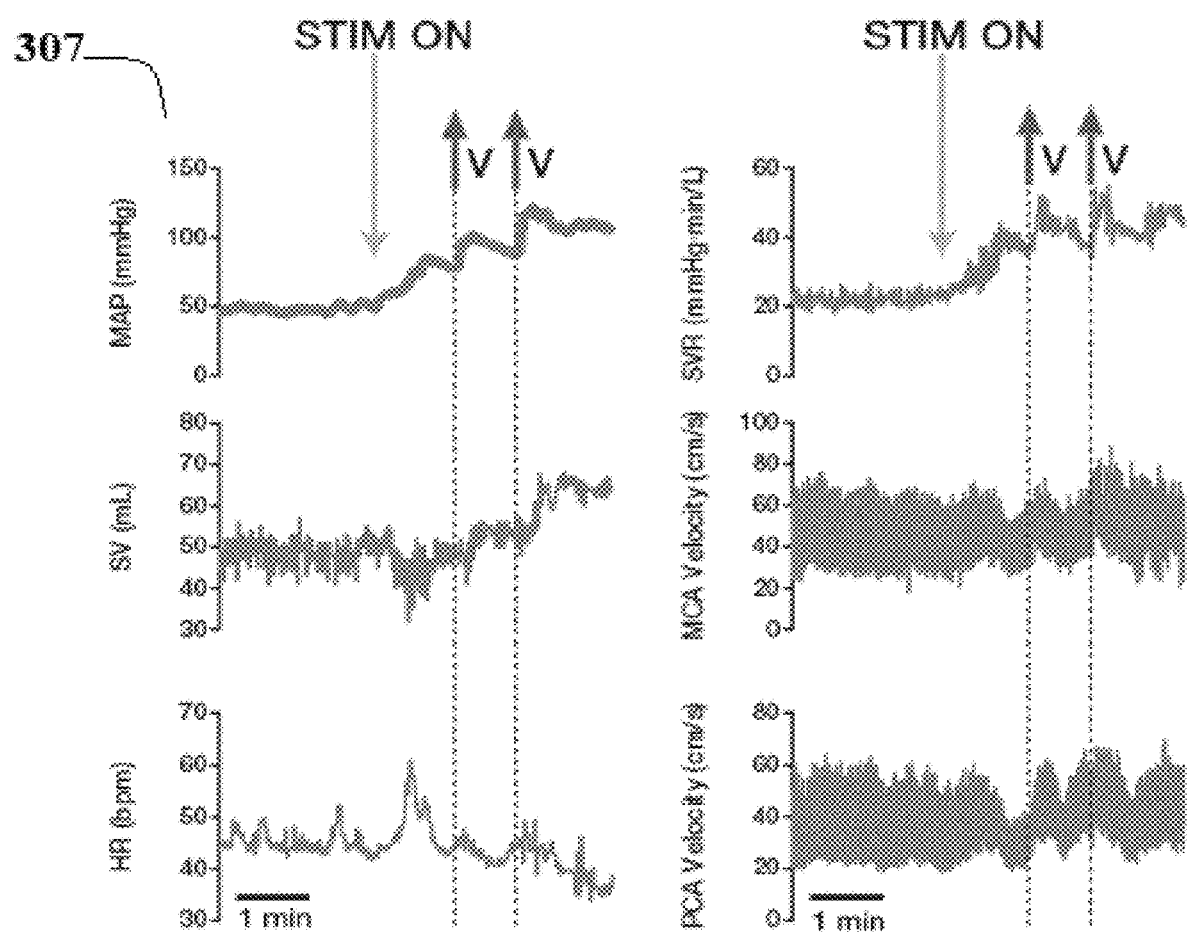
Figure 3E:
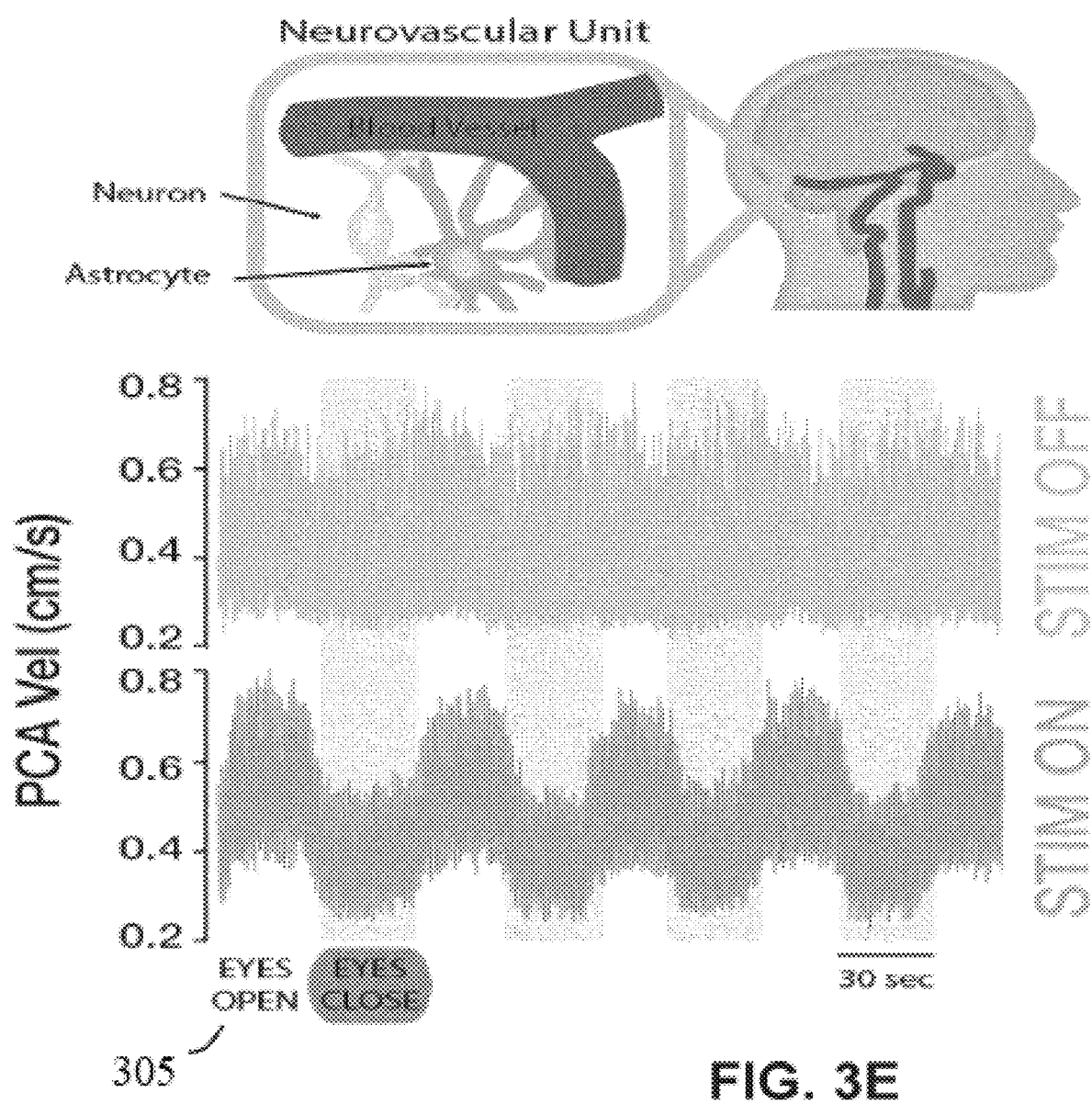
Figure 3F:
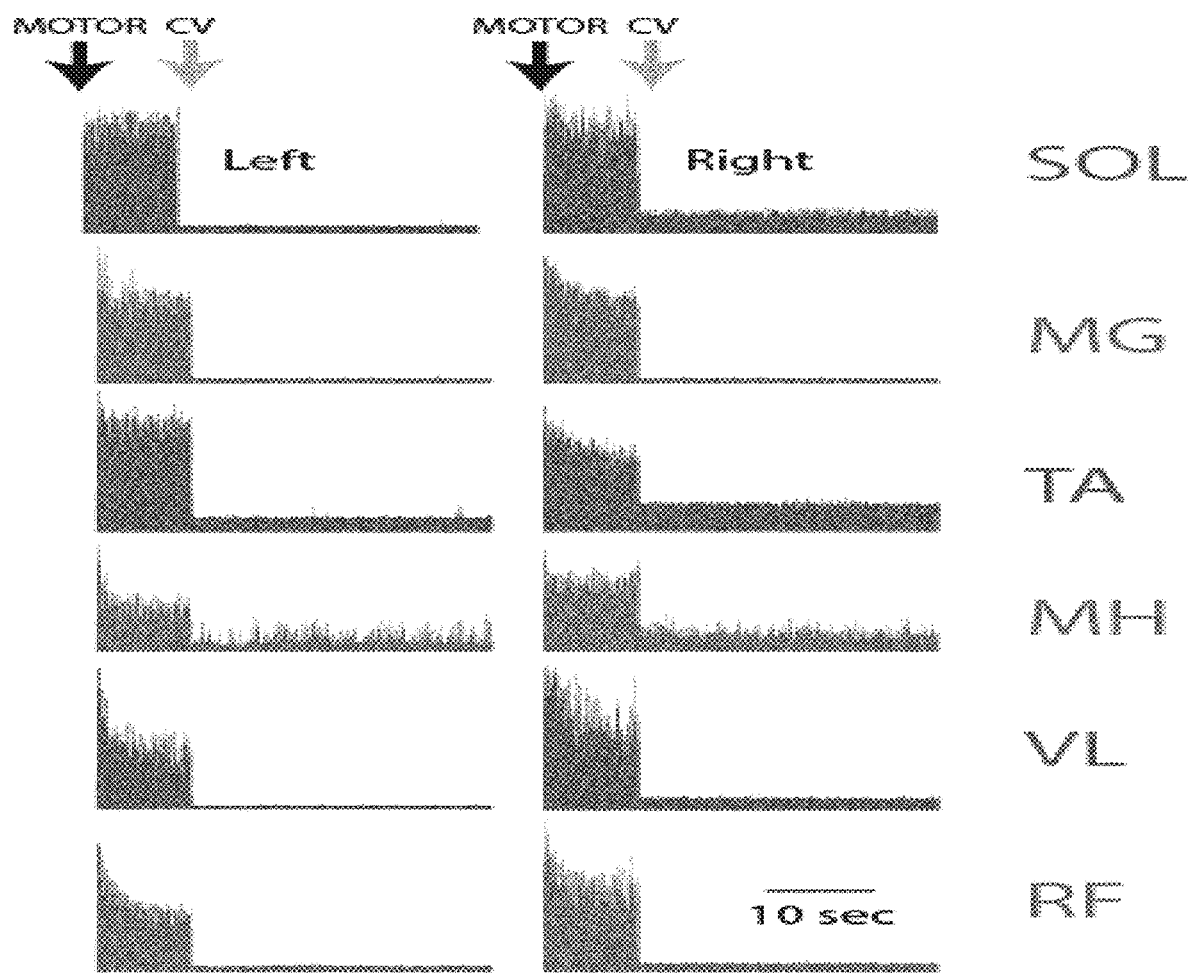
Figure 3G:
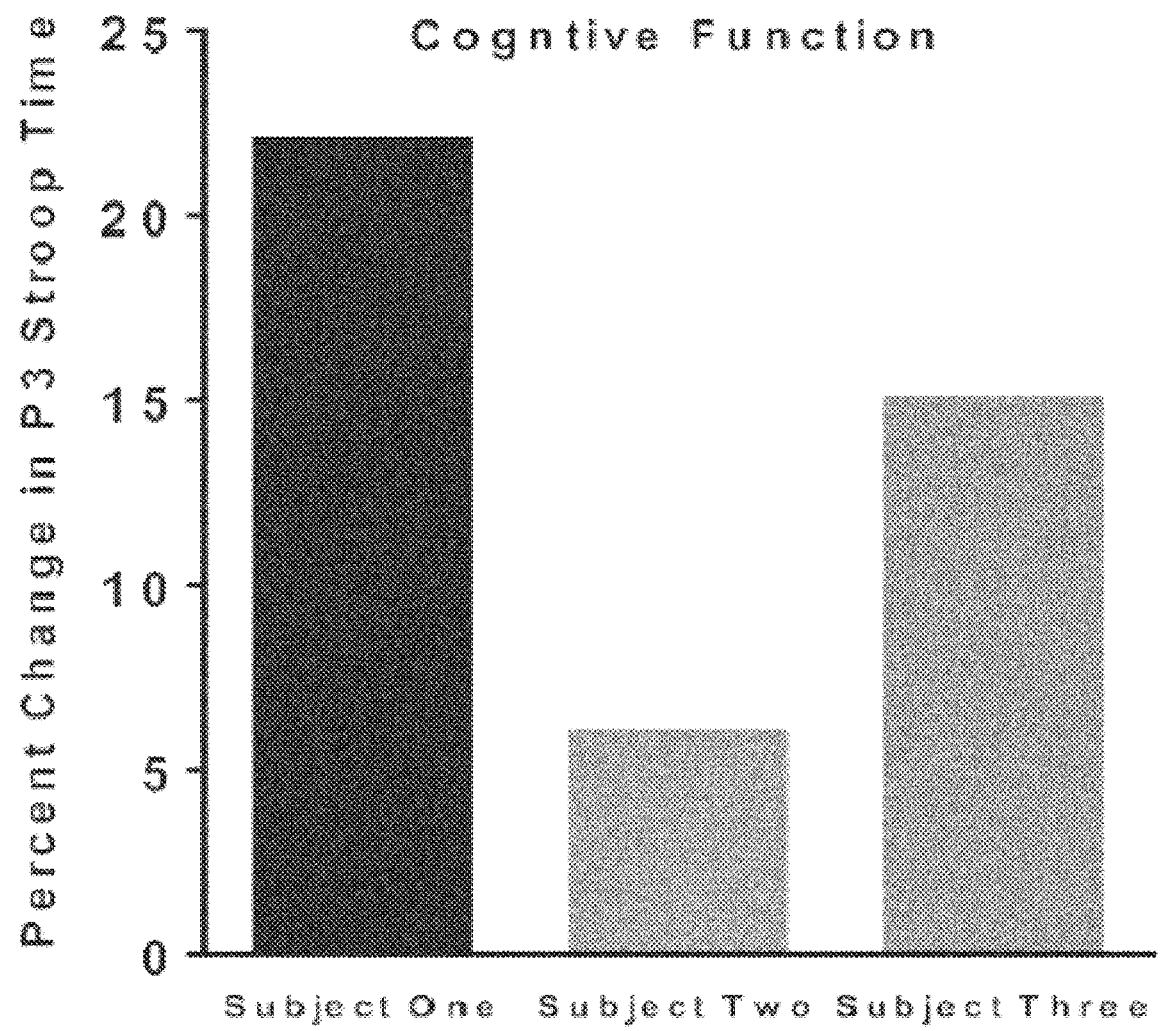

Raw echocardiography imaging 303 in FIG. 3C of the left-ventricular outflow tract in the seated position demonstrates that peak outflow velocity and cardiac output are increased with stimulation.

Model-flow estimations 307 of mean arterial blood pressure, stroke volume, heart rate and systemic vascular resistance obtained from finger plethysmography along with raw transcranial Doppler images of the mid cerebral artery (MCA) and the posterior cerebral artery (PCA). Note the stepwise increase in all variables when the stimulator was activated (V), except heart rate which was offset due to the associated increase in stroke volume.

Raw changes in PCA velocity in response to cerebral activation (eyes open) 305 indicate the complete restoration of neurovascular coupling with stimulation (i.e., appropriate regulation of PCA velocity with cerebral activation). Lower-limb electromyography responses 305 to both low-frequency 'motor-optimized' and high-frequency 'cardiovascular-optimized' epidural stimulation reveal no concurrent motor activity during CV-optimized stimulation.

Figure 4D:
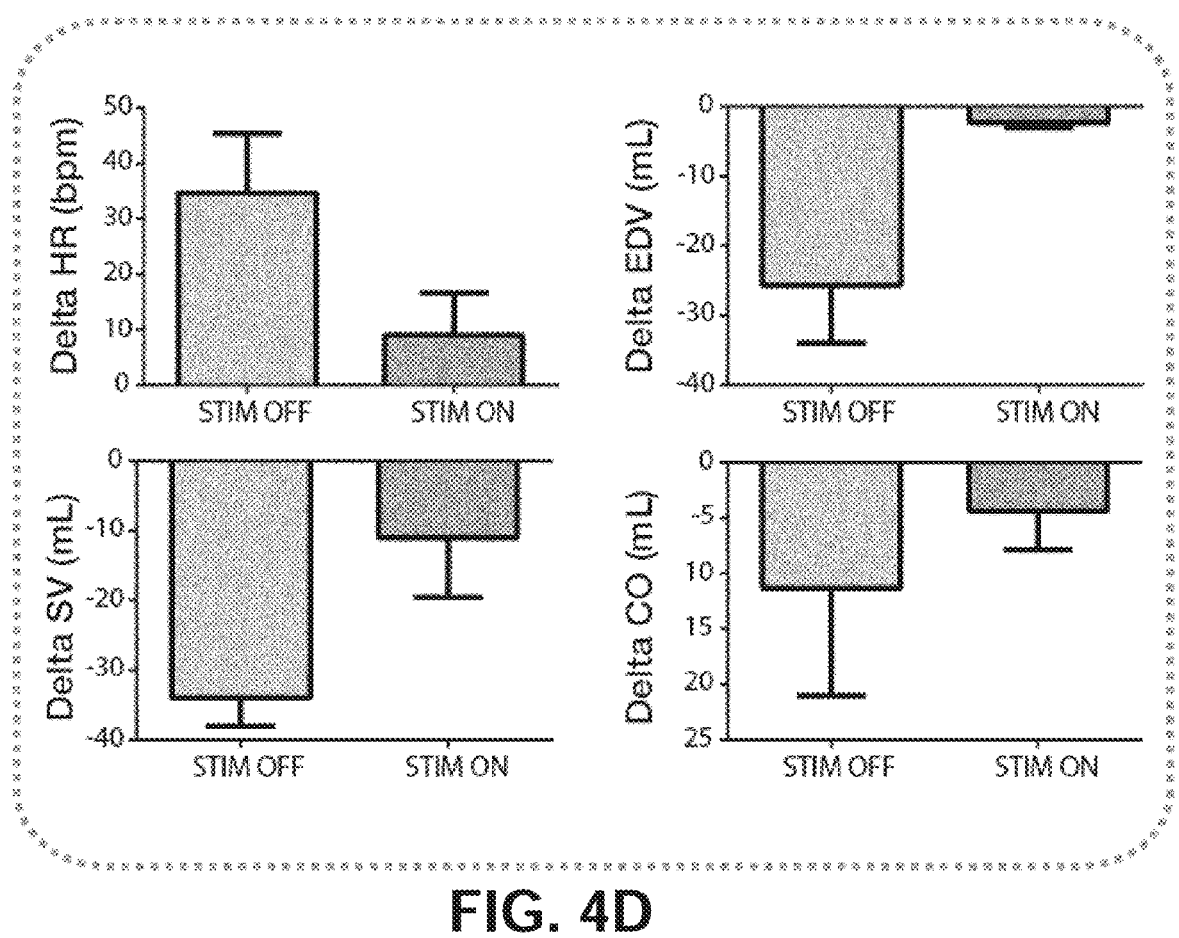

Example 2: Cardiovascular Optimized Epidural Stimulation Improved Multiple Facets of Cardiovascular Function in all Three Study Participants FIG. 4A illustrates the improvements to cardiovascular function following controlled electrical stimulation in individuals with SCI. FIGS. 4B to 4D are enlarged views of portions of FIG. 4A. FIG. 4B shows Systolic blood pressure (SBP), posterior cerebral artery velocity (PCA), and mid cerebral artery (MCA) velocity were all maintained with stimulation in response to a 10 minute sit-up test. Stimulation increased low-frequency oscillations in SBP while in the seated position, indicating a return of supraspinal cardiovascular control. FIG. 4A (top right) shows changes in posterior cerebral artery blood flow in response to neural activation using a classical eyes-closed eyes-open task indicate that stimulation restored neurovascular coupling in all individuals (i.e., there was an appropriate increase in PCA flow in response to neural activation with stimulation), which was virtually absent without stimulation. FIG. 4D shows: echocardiography-derived cardiac responses to orthostatic challenge indicate that stimulation prevented the decline in end-diastolic volume (EDV), stroke volume (SV) and cardiac output (CO) noted without stimulation; consequently, there was also a reduction in the magnitude of orthostatic-induced tachycardia with stimulation. Also shown are the group mean±SD for the major cardiac variables summarized in panel.

Figure 5A:
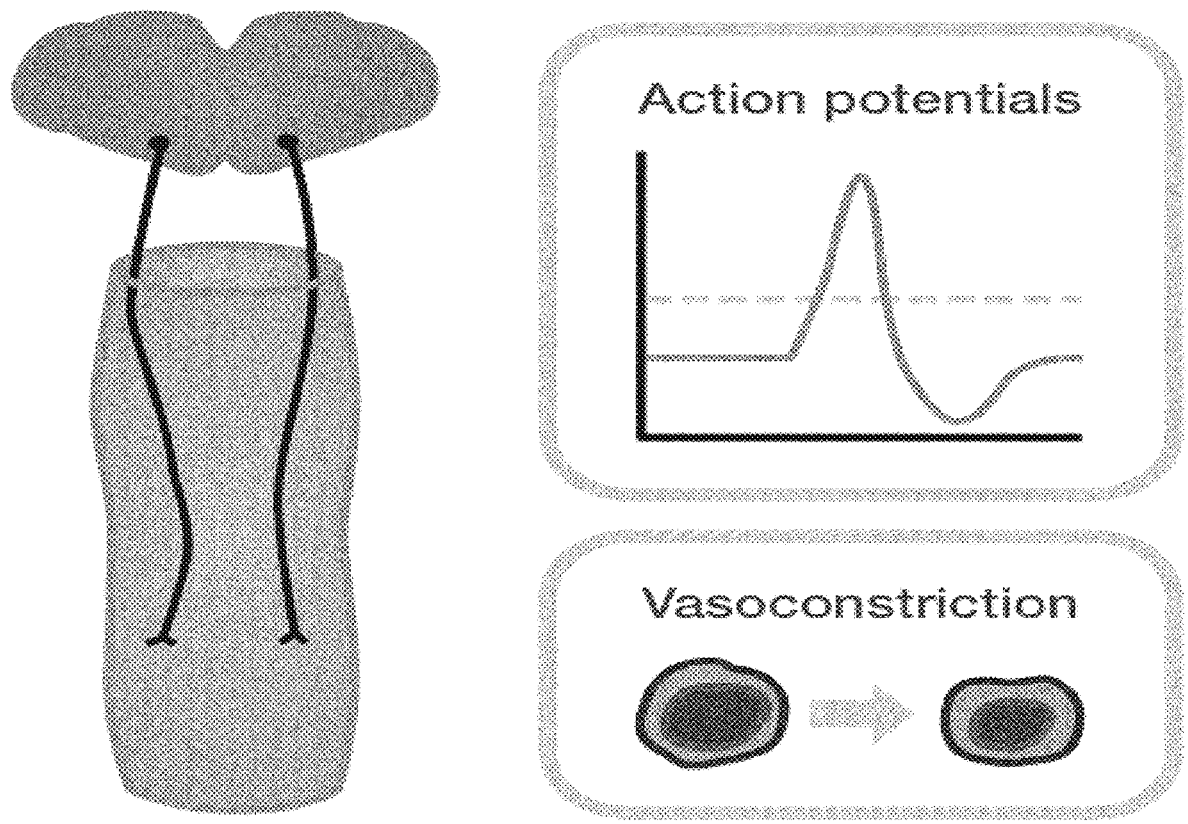
FIGS. 5A to 5C demonstrate how potentiation of sympathetic circuitry may restore dormant sympathetic cardiovascular pathways.
Figure 5B:
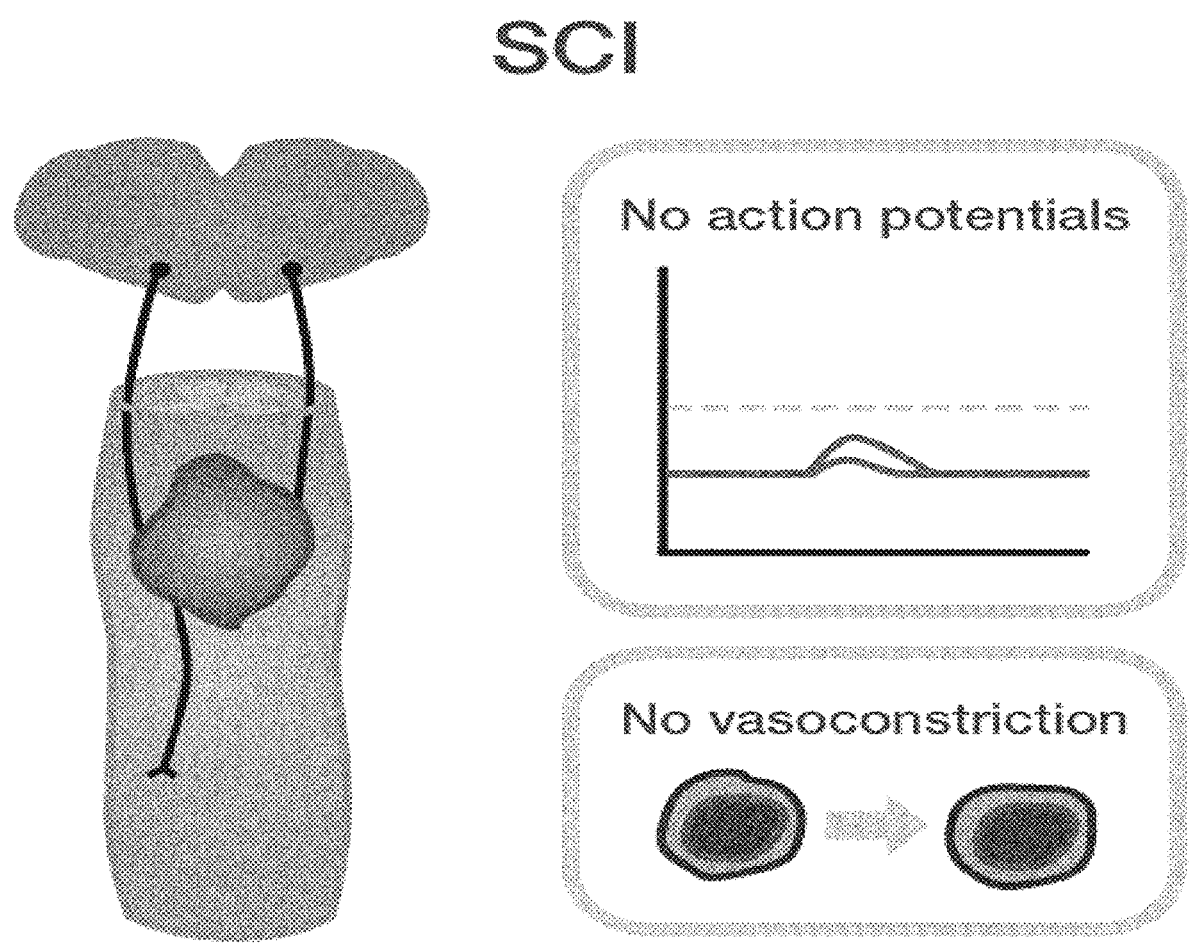
Figure 5C:
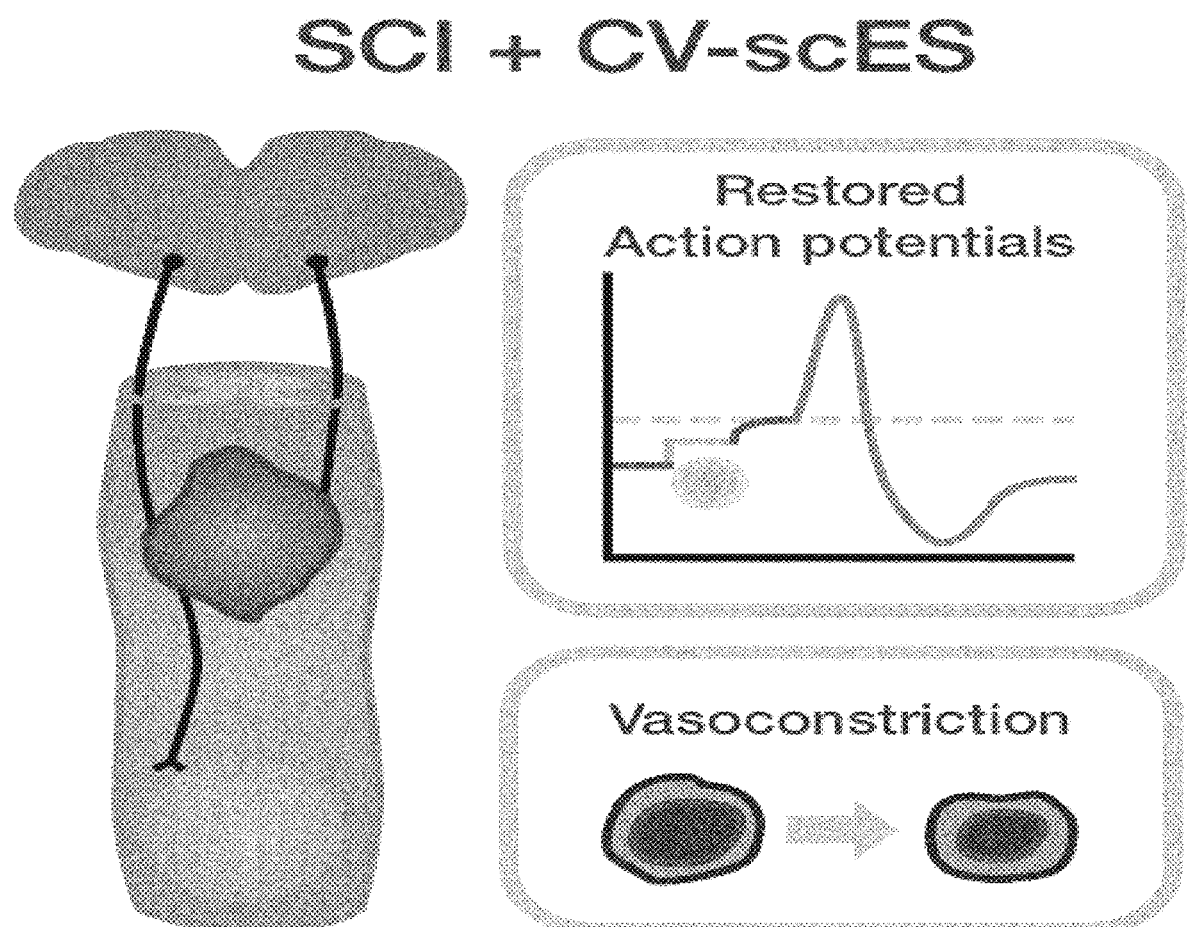
Figure 7:
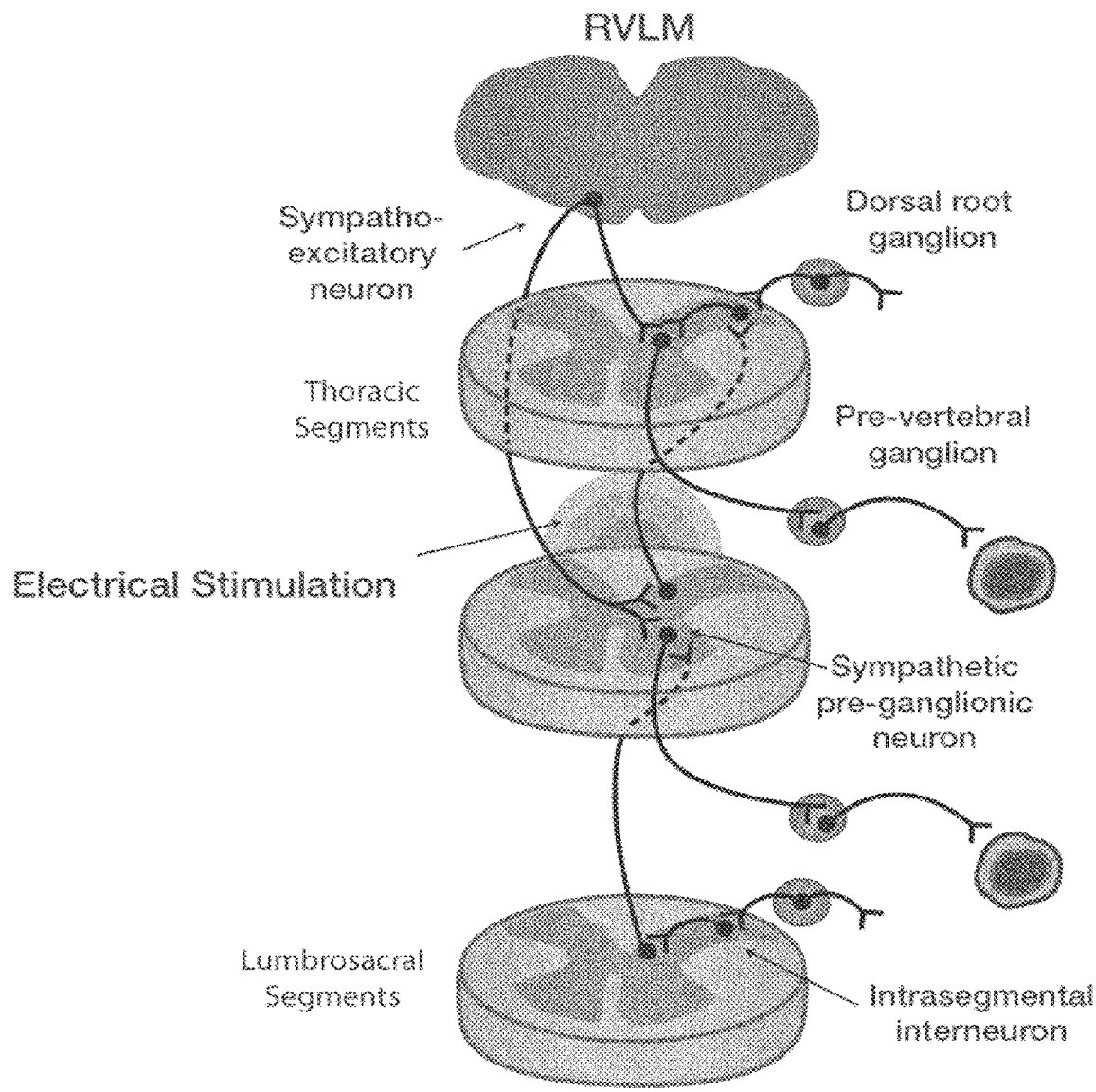
FIG. 7 illustrates a theoretical framework of transcutaneous stimulation.

Example 3: Theoretical Restoration of Dormant Supraspinal Descending Sympathetic Cardiovascular Pathways Through Potentiation of Caudal Sympathetic Circuitry FIGS. 5A to 5C show how cardiovascular functioning may be restored in individuals with SCI following controlled electrical stimulation. FIG. 5A shows descending sympathetic pathways from the rostral ventrolateral medulla (RVLM) in an intact spinal cord may lead to efficacious action potentials (i.e., depolarization) in sympathetic circuitry that allow for supraspinal control over vascular tone (i.e., vasoconstriction) and blood pressure. FIG. 5B shows how interrupted descending sympathetic pathways due to an anatomically discomplete SCI, where a small number of preserved descending sympathetic fibres crossing the site of injury are not capable of eliciting action potentials in sympathetic circuitry caudal to injury. FIG. 5C illustrates that epidural spinal electrical stimulation increases the resting membrane potential of sympathetic circuitry caudal to the spinal cord injury allowing for the previously non-efficacious preserved descending sympathetic fibres crossing the site of injury to actively regulate caudal sympathetic circuits, and thereby restore supraspinal control of vascular tone and blood pressure. As shown in FIG. 7, epidural electrical stimulation may stimulate dorsal afferents that likely affect the membrane potential of intersegmental and intrasegmental neurons, that: 1) receive direct input from descending sympathetic pathways, and 2) directly and indirectly lead to depolarization of sympathetic preganglionic neurons leading to regulation of vascular tone.

Figure 6:
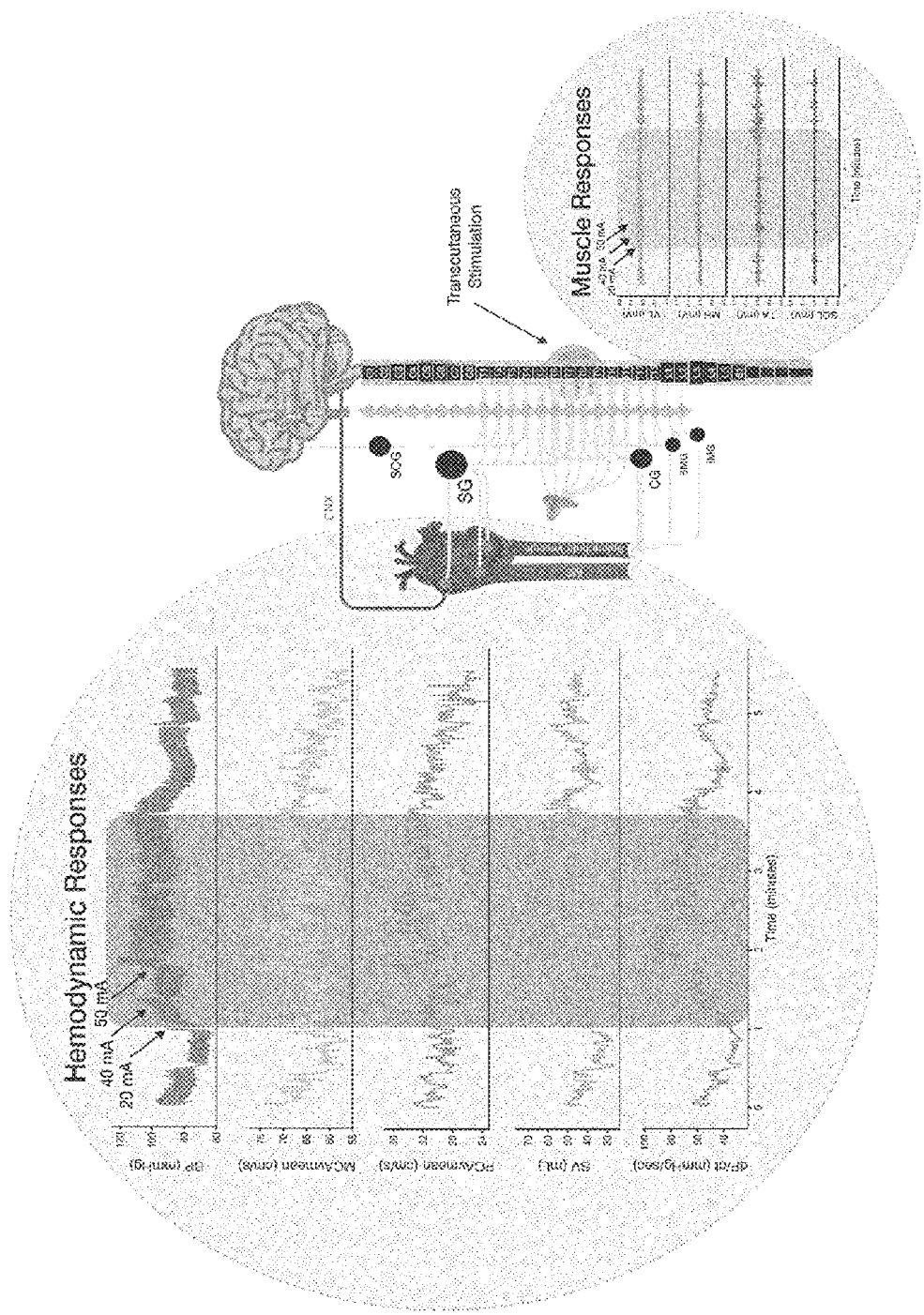
FIG. 6 illustrates improved integrated cardiovascular responses to orthostatic challenge in an individual resulting from thoracic electrical stimulation.

Example 4: Thoracic Electrical Transcutaneous Stimulation Improved Integrated Cardiovascular Responses to Orthostatic Challenge FIG. 6 shows improvements to cardiovascular function following controlled transcutaneous electrical stimulation in an individual with SCI. Participant: Female, 32 years of age, spinal cord injury at C6 (AIS-A), injured August 2009. Left Inlet: Although suffering from severe orthostatic hypotension when assuming upright posture, electrical stimulation at the TVII level restored blood pressure, cerebral blood flow, cardiac function, and symptoms of orthostatic intolerance to supine levels. Note: Increasing current (from 20 mA, to 40 mA, to 50 mA) resulted in step-wise increases in cardiovascular function. Right Inlet: electromyography recording of lower-limbs shows that skeletal muscle contraction was not activating the skeletal muscle pump of the venous vasculature, indicating that excitation of sympathetic preganglionic neurons was responsible for the cardiovascular restoration. Note: Without stimulation self-reported symptoms of presyncope were severe, being between 6-9, while with stimulation symptoms were completely abrogated. Participant reported that cognitive processing was so slow in the upright position that she was "not conversational" until the stimulation was turned on.

Example 5: Theoretical Framework of Transcutaneous Stimulation

FIG. 7 shows how thoracic level stimulation using transcutaneous electrical stimulation excites dorsal afferents that likely excite intersegmental and intrasegmental neurons, which directly and indirectly lead to depolarization of sympathetic preganglionic neurons leading to increased vascular tone.

Interpretation of Terms

Unless the context clearly requires otherwise, throughout the description and the claims:
  "comprise", "comprising", and the like are to be construed in an inclusive sense, as opposed to an exclusive or exhaustive sense; that is to say, in the sense of "including, but not limited to";
  "connected", "coupled", or any variant thereof, means any connection or coupling, either direct or indirect, between two or more elements; the coupling or connection between the elements can be physical, logical, or a combination thereof;
  "herein", "above", "below", and words of similar import, when used to describe this specification, shall refer to this specification as a whole, and not to any particular portions of this specification;
  "or", in reference to a list of two or more items, covers all of the following interpretations of the word: any of the items in the list, all of the items in the list, and any combination of the items in the list;
  the singular forms "a", "an", and "the" also include the meaning of any appropriate plural forms.
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

The following abbreviations have the following meanings:
  BP, blood pressure.
  CG, celiac ganglia
  CO, cardiac output.
  DBP, diastolic blood pressure.
  dP/dt, delta pressure over delta time (cardiac contractility).
  EDV end-diastolic volume.
  HR, heart rate.
  IMG, inferior mesenteric ganglia.
  MCA mid cerebral artery.
  MH, medial hamstring.
  PCA, posterior cerebral artery.
  PCAvmean, mean flow velocity for PCA.
  RVLM, rostral ventrolateral medulla.
  SBP, systolic blood pressure.
  SCG, superior cervical ganglia.

SCI, spinal cord injury.
SG, stellate ganglia.
SMG, superior mesenteric ganglia.
SOL, soleus.
SV, stroke volume.
TA, tibialis anterior.
VL, vastus lateralis.
vmean, mean flow velocity.

The disclosure may also be provided in the form of a program product. The program product may comprise any non-transitory medium which carries a set of computer-readable instructions which, when executed by a data processor, cause the data processor to execute a method of the disclosure (e.g. a method as illustrated in FIG. 2A or FIG. 2B). Program products according to the disclosure may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the disclosure may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the disclosure.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this disclosure. This disclosure includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Various features are described herein as being present in "some embodiments". Such features are not mandatory and may not be present in all embodiments. Embodiments of the disclosure may include zero, any one or any combination of two or more of such features. This is limited only to the extent that certain ones of such features may be incompatible with other ones of such features in the sense that it would be impossible for a person of ordinary skill in the art to construct a practical embodiment that combines such incompatible features. Consequently, separate or combined statements in the description that "some embodiments" possess feature A and "some embodiments" possess feature B should be interpreted as an express indication that the disclosure also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the embodiments set forth in the examples, but should be given the broadest interpretation consistent with the description as a whole.

The invention claimed is:

1. An apparatus for controlling blood pressure in a subject, the apparatus comprising:
    an input for receiving a BP signal indicative of a blood pressure measurement;
    a feedback control circuit connected to a sensor to receive the BP signal from the input and to deliver a stimulation control signal to an output, the feedback control circuit configured to:
        compare the blood pressure measurement to a target blood pressure range, wherein
        if the comparison indicates that the blood pressure measurement is below the target blood pressure range increase a level of the stimulation control signal until the blood pressure measurement is in the target blood pressure range; and
        if the comparison indicates that the blood pressure measurement is above the target blood pressure range decrease a level of the stimulation control signal until the blood pressure measurement is in the target blood pressure range;
    wherein the apparatus comprises a processor configured to receive a measurement of bladder function and to control blood pressure and at least one of bladder and bowel function by respectively applying a blood pressure stimulation signal and a bladder/bowel stimulation signal;
    wherein the blood pressure stimulation signal and bladder/bowel stimulation signal are different from one another;
    wherein the blood pressure stimulation signal and bladder/bowel stimulation signal are electrical signals and the blood pressure stimulation signal and bladder/bowel stimulation signal are delivered using different sets of electrodes of an electrode array implanted adjacent to a subject's spinal cord; and
    wherein the measurement of bladder function is a measure of bladder volume.

2. The apparatus according to claim 1, wherein the feedback control circuit stores an increment value and a lag time and is configured to increase the level of the stimulation control signal until the blood pressure measurement is in the target blood pressure range by repeatedly increasing the level of the stimulation control signal by the increment value, waiting for the lag time, obtaining a new blood pressure measurement from the input and comparing the new blood pressure measurement to the target blood pressure range.

3. The apparatus according to claim 2, wherein the lag time is between a few seconds to 15 minutes.

4. The apparatus according to claim 1, wherein the stimulation control signal is continuously applied and the level of the stimulation control signal is adjusted based on the blood pressure measurement.

5. The apparatus according to claim 1, further comprising an electrical pulse generator connected to receive the stimulation control signal and to generate electrical pulses and apply the generated electrical pulses to an electrode array, wherein increasing the level of the stimulation control signal causes the electrical pulse generator to increase a voltage and/or a current and/or a frequency and/or a pulse width of generated electrical pulses.

6. The apparatus according to claim 5, wherein the electrode array comprises a transdermal electrode array and the stimulation control signal controls for a stimulation output comprising a voltage between about 0.1 V to about 100 V and an amperage between about 0 mA to about 100 mA.

7. The apparatus according to claim 5, wherein the electrode array comprises an epidural electrode array and the stimulation control signal controls for a stimulation output comprising a voltage between about 0.1 V to about 20 V and an amperage between about 0 mA to about 100 mA.

8. The apparatus according to claim 5, wherein the stimulation control signal controls for a stimulation output comprising electrical pulses presented at a pulse frequency between about 5 Hz to 10 kHz.

9. The apparatus according to claim 5, wherein the stimulation control signal controls for a stimulation output comprising electrical pulses having a pulse width between about 0.002 seconds to about 20 seconds.

10. The apparatus according to claim 9, wherein the pulse width is between about 0.033 seconds to about 0.17 seconds.

11. The apparatus according to claim 5, wherein the electrode array is a transdermal electrode array or an epidural electrode array.

12. The apparatus according to claim 1, further comprising a user control, wherein activation of the user control triggers the apparatus to deliver the bladder/bowel stimulation signal.

13. The apparatus according to claim 12, wherein the apparatus is configured to interrupt or inhibit delivery of the blood pressure stimulation signal while delivering the bladder/bowel stimulation signal.

14. The apparatus according to claim 1, wherein the blood pressure measurement is a systolic measurement.

15. A method for operating an apparatus to control a subject's blood pressure, the method comprising:

receiving at the apparatus a signal containing a blood pressure measurement indicative of the subject's blood pressure;

comparing the blood pressure measurement to a predetermined target range stored in a data store accessible to the apparatus; wherein if the comparison indicates that the blood pressure measurement is below the target blood pressure range increasing a level of a stimulation control signal until the blood pressure measurement is in the target blood pressure range; and if the comparison indicates that the blood pressure measurement is above the target blood pressure range decreasing the level of the stimulation control signal until the blood pressure measurement is in the target blood pressure range;

wherein the apparatus is connected to receive a measurement of bladder function and is configured to control blood pressure and one or both of bladder and bowel function by respectively applying a blood pressure stimulation signal and a bladder/bowel stimulation signal;

wherein the blood pressure stimulation signal and bladder/bowel stimulation signal are different from one another;

wherein the blood pressure stimulation signal and bladder/bowel stimulation signal are electrical signals and the blood pressure stimulation signal and bladder/bowel stimulation signal are delivered using different sets of electrodes of an electrode array implanted adjacent to a subject's spinal cord; and wherein the measurement of bladder function is a measure of bladder volume.

16. The method according to claim 15, wherein when the comparison indicates that the blood pressure measurement is below the target blood pressure range, increasing the level of the stimulation control signal until the blood pressure measurement is in the target blood pressure range by repeatedly increasing the level of the stimulation control signal by an increment value, waiting for a lag time, obtaining a new blood pressure measurement and comparing the new blood pressure measurement to the target blood pressure range.

17. The method according to claim 16, wherein the lag time is between a few seconds to 15 minutes.

18. The method according to claim 15, wherein the stimulation control signal controls a continuous stimulation and the level of the stimulation control signal is iteratively adjusted based on the blood pressure measurement.

19. The method according to claim 15, wherein the stimulation control signal is connected to control an electrical pulse generator to generate electrical pulses, wherein increasing the level of the stimulation control signal causes the electrical pulse generator to increase a voltage and/or a current and/or a frequency and/or a pulse width of the generated electrical pulses.

20. The method according to claim 15, wherein the blood pressure measurement is a systolic measurement.

* * * * *